(12) United States Patent
Al-Ali et al.

(10) Patent No.: US 11,645,905 B2
(45) Date of Patent: *May 9, 2023

(54) SYSTEMS AND METHODS FOR MONITORING A PATIENT HEALTH NETWORK

(71) Applicant: MASIMO CORPORATION, Irvine, CA (US)

(72) Inventors: Yaser Ammar Al-Ali, San Juan Capistrano, CA (US); Jad Adel Wafeeq, Mission Viejo, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/861,022

(22) Filed: Apr. 28, 2020

(65) Prior Publication Data
US 2020/0394903 A1 Dec. 17, 2020

Related U.S. Application Data

(63) Continuation of application No. 15/948,546, filed on Apr. 9, 2018, now Pat. No. 10,672,260, which is a
(Continued)

(51) Int. Cl.
*G08C 17/02* (2006.01)
*G16H 40/40* (2018.01)
(Continued)

(52) U.S. Cl.
CPC .............. *G08C 17/02* (2013.01); *G06F 11/00* (2013.01); *G06F 11/30* (2013.01); *G16H 40/40* (2018.01); *G05B 23/0283* (2013.01)

(58) Field of Classification Search
CPC ........ G08C 17/02; G16H 40/40; G16H 40/00; G05B 23/0283; G06Q 10/20;
(Continued)

(56) References Cited

U.S. PATENT DOCUMENTS 4,960,128 A 10/1990 Gordon et al.
4,964,408 A 10/1990 Hink et al.
(Continued)

FOREIGN PATENT DOCUMENTS

WO WO 01/034023 5/2001
WO WO 03/054704 7/2003
WO WO 2005/010756 2/2005

OTHER PUBLICATIONS

US 2022/0192529 A1, 06/2022, Al-Ali et al. (withdrawn)
(Continued)

*Primary Examiner* — Brian Wilson
(74) *Attorney, Agent, or Firm* — Knobbe Martens Olson & Bear LLP

(57) ABSTRACT

Systems and methods for monitoring physiological monitoring systems are described herein. A communication interface module can be configured to receive from a physiological monitoring system first data based on a snapshot taken of a status of the physiological monitoring system at a first time. A memory module can be configured to store the first data and a baseline associated with the physiological monitoring system. A processor module can be configured to compare the first data with the baseline and to generate a notification if the first data deviates from the baseline by a predetermined amount. A display module can be configured to display a physical location of a plurality of physiological monitoring systems and display the notification.

20 Claims, 17 Drawing Sheets

Related U.S. Application Data continuation of application No. 14/198,350, filed on Mar. 5, 2014, now Pat. No. 9,965,946.

(60) Provisional application No. 61/780,794, filed on Mar. 13, 2013.

(51) Int. Cl.
*G06F 11/00* (2006.01)
*G06F 11/30* (2006.01)
*G05B 23/02* (2006.01)

(58) Field of Classification Search
CPC ........ G06F 3/0482; G06F 11/00; G06F 11/07;
G06F 11/22; G06F 11/2247; G06F
11/2294; G06F 11/30; G06F 11/3006;
G06F 11/3055; G06F 11/3065; G06F
11/3082; G06F 11/32; G06F 11/327;
G06F 11/34; G06F 11/3409; G06F
11/3442; G06F 11/3466; G06F 19/00;
G06F 19/322; G06F 19/327; G06F
19/3406; G06F 19/3412; G06F 19/3418;
G06F 11/3447; G06F 11/3452; G06F
11/3476; G06F 2201/81
USPC ... 340/870.01, 870.09, 539.1, 539.12, 573.1;
700/28, 32, 108, 109
See application file for complete search history.

(56) References Cited

U.S. PATENT DOCUMENTS

| | | | |
|---|---|---|---|
| 5,041,187 A | 8/1991 | Hink et al. |
| 5,069,213 A | 12/1991 | Hink et al. |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,865,832 A | 2/1999 | Knopp et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |

(56) References Cited

U.S. PATENT DOCUMENTS

| | | | |
|---|---|---|---|
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |

(56) References Cited

U.S. PATENT DOCUMENTS

| | | |
|---|---|---|
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfire et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |

(56) References Cited

U.S. PATENT DOCUMENTS

| | | | |
|---|---|---|---|
| 8,588,880 | B2 | 11/2013 | Abdul-Hafiz et al. |
| 8,600,467 | B2 | 12/2013 | Al-Ali et al. |
| 8,606,342 | B2 | 12/2013 | Diab |
| 8,626,255 | B2 | 1/2014 | Al-Ali et al. |
| 8,630,691 | B2 | 1/2014 | Lamego et al. |
| 8,634,889 | B2 | 1/2014 | Al-Ali et al. |
| 8,641,631 | B2 | 2/2014 | Sierra et al. |
| 8,652,060 | B2 | 2/2014 | Al-Ali |
| 8,663,107 | B2 | 3/2014 | Kiani |
| 8,666,468 | B1 | 3/2014 | Al-Ali |
| 8,667,967 | B2 | 3/2014 | Al-Ali et al. |
| 8,670,811 | B2 | 3/2014 | O'Reilly |
| 8,670,814 | B2 | 3/2014 | Diab et al. |
| 8,676,286 | B2 | 3/2014 | Weber et al. |
| 8,682,407 | B2 | 3/2014 | Al-Ali |
| RE44,823 | E | 4/2014 | Parker |
| RE44,875 | E | 4/2014 | Kiani et al. |
| 8,688,183 | B2 | 4/2014 | Bruinsma et al. |
| 8,690,799 | B2 | 4/2014 | Telfort et al. |
| 8,700,112 | B2 | 4/2014 | Kiani |
| 8,702,627 | B2 | 4/2014 | Telfort et al. |
| 8,706,179 | B2 | 4/2014 | Parker |
| 8,712,494 | B1 | 4/2014 | MacNeish, III et al. |
| 8,715,206 | B2 | 5/2014 | Telfort et al. |
| 8,718,735 | B2 | 5/2014 | Lamego et al. |
| 8,718,737 | B2 | 5/2014 | Diab et al. |
| 8,718,738 | B2 | 5/2014 | Blank et al. |
| 8,720,249 | B2 | 5/2014 | Al-Ali |
| 8,721,541 | B2 | 5/2014 | Al-Ali et al. |
| 8,721,542 | B2 | 5/2014 | Al-Ali et al. |
| 8,723,677 | B1 | 5/2014 | Kiani |
| 8,740,792 | B1 | 6/2014 | Kiani et al. |
| 8,754,776 | B2 | 6/2014 | Poeze et al. |
| 8,755,535 | B2 | 6/2014 | Telfort et al. |
| 8,755,856 | B2 | 6/2014 | Diab et al. |
| 8,755,872 | B1 | 6/2014 | Marinow |
| 8,761,850 | B2 | 6/2014 | Lamego |
| 8,764,671 | B2 | 7/2014 | Kiani |
| 8,768,423 | B2 | 7/2014 | Shakespeare et al. |
| 8,771,204 | B2 | 7/2014 | Telfort et al. |
| 8,777,634 | B2 | 7/2014 | Kiani et al. |
| 8,781,543 | B2 | 7/2014 | Diab et al. |
| 8,781,544 | B2 | 7/2014 | Al-Ali et al. |
| 8,781,549 | B2 | 7/2014 | Al-Ali et al. |
| 8,788,003 | B2 | 7/2014 | Schurman et al. |
| 8,790,268 | B2 | 7/2014 | Al-Ali |
| 8,801,613 | B2 | 8/2014 | Al-Ali et al. |
| 8,821,397 | B2 | 9/2014 | Al-Ali et al. |
| 8,821,415 | B2 | 9/2014 | Al-Ali et al. |
| 8,830,449 | B1 | 9/2014 | Lamego et al. |
| 8,831,700 | B2 | 9/2014 | Schurman et al. |
| 8,840,549 | B2 | 9/2014 | Al-Ali et al. |
| 8,847,740 | B2 | 9/2014 | Kiani et al. |
| 8,849,365 | B2 | 9/2014 | Smith et al. |
| 8,852,094 | B2 | 10/2014 | Al-Ali et al. |
| 8,852,994 | B2 | 10/2014 | Wojtczuk et al. |
| 8,868,147 | B2 | 10/2014 | Stippick et al. |
| 8,868,150 | B2 | 10/2014 | Al-Ali et al. |
| 8,870,792 | B2 | 10/2014 | Al-Ali et al. |
| 8,886,271 | B2 | 11/2014 | Kiani et al. |
| 8,888,539 | B2 | 11/2014 | Al-Ali et al. |
| 8,888,708 | B2 | 11/2014 | Diab et al. |
| 8,892,180 | B2 | 11/2014 | Weber et al. |
| 8,897,847 | B2 | 11/2014 | Al-Ali |
| 8,909,310 | B2 | 12/2014 | Lamego et al. |
| 8,911,377 | B2 | 12/2014 | Al-Ali |
| 8,912,909 | B2 | 12/2014 | Al-Ali et al. |
| 8,920,317 | B2 | 12/2014 | Al-Ali et al. |
| 8,921,699 | B2 | 12/2014 | Al-Ali et al. |
| 8,922,382 | B2 | 12/2014 | Al-Ali et al. |
| 8,929,964 | B2 | 1/2015 | Al-Ali et al. |
| 8,942,777 | B2 | 1/2015 | Diab et al. |
| 8,948,834 | B2 | 2/2015 | Diab et al. |
| 8,948,835 | B2 | 2/2015 | Diab |
| 8,965,471 | B2 | 2/2015 | Lamego |
| 8,983,564 | B2 | 3/2015 | Al-Ali |
| 8,989,831 | B2 | 3/2015 | Al-Ali et al. |
| 8,996,085 | B2 | 3/2015 | Kiani et al. |
| 8,998,809 | B2 | 4/2015 | Kiani |
| 9,028,429 | B2 | 5/2015 | Telfort et al. |
| 9,037,207 | B2 | 5/2015 | Al-Ali et al. |
| 9,060,721 | B2 | 6/2015 | Reichgott et al. |
| 9,066,666 | B2 | 6/2015 | Kiani |
| 9,066,680 | B1 | 6/2015 | Al-Ali et al. |
| 9,072,474 | B2 | 7/2015 | Al-Ali et al. |
| 9,078,560 | B2 | 7/2015 | Schurman et al. |
| 9,084,569 | B2 | 7/2015 | Weber et al. |
| 9,095,316 | B2 | 8/2015 | Welch et al. |
| 9,106,038 | B2 | 8/2015 | Telfort et al. |
| 9,107,625 | B2 | 8/2015 | Telfort et al. |
| 9,107,626 | B2 | 8/2015 | Al-Ali et al. |
| 9,113,831 | B2 | 8/2015 | Al-Ali |
| 9,113,832 | B2 | 8/2015 | Al-Ali |
| 9,119,595 | B2 | 9/2015 | Lamego |
| 9,131,881 | B2 | 9/2015 | Diab et al. |
| 9,131,882 | B2 | 9/2015 | Al-Ali et al. |
| 9,131,883 | B2 | 9/2015 | Al-Ali |
| 9,131,917 | B2 | 9/2015 | Telfort et al. |
| 9,138,180 | B1 | 9/2015 | Coverston et al. |
| 9,138,182 | B2 | 9/2015 | Al-Ali et al. |
| 9,138,192 | B2 | 9/2015 | Weber et al. |
| 9,142,117 | B2 | 9/2015 | Muhsin et al. |
| 9,153,112 | B1 | 10/2015 | Kiani et al. |
| 9,153,121 | B2 | 10/2015 | Kiani et al. |
| 9,161,696 | B2 | 10/2015 | Al-Ali et al. |
| 9,161,713 | B2 | 10/2015 | Al-Ali et al. |
| 9,167,995 | B2 | 10/2015 | Lamego et al. |
| 9,176,141 | B2 | 11/2015 | Al-Ali et al. |
| 9,186,102 | B2 | 11/2015 | Bruinsma et al. |
| 9,192,312 | B2 | 11/2015 | Al-Ali |
| 9,192,329 | B2 | 11/2015 | Al-Ali |
| 9,192,351 | B1 | 11/2015 | Telfort et al. |
| 9,195,385 | B2 | 11/2015 | Al-Ali et al. |
| 9,211,072 | B2 | 12/2015 | Kiani |
| 9,211,095 | B1 | 12/2015 | Al-Ali |
| 9,218,454 | B2 | 12/2015 | Kiani et al. |
| 9,226,696 | B2 | 1/2016 | Kiani |
| 9,241,662 | B2 | 1/2016 | Al-Ali et al. |
| 9,245,668 | B1 | 1/2016 | Vo et al. |
| 9,259,185 | B2 | 2/2016 | Abdul-Hafiz et al. |
| 9,267,572 | B2 | 2/2016 | Barker et al. |
| 9,277,880 | B2 | 3/2016 | Poeze et al. |
| 9,289,167 | B2 | 3/2016 | Diab et al. |
| 9,295,421 | B2 | 3/2016 | Kiani et al. |
| 9,307,928 | B1 | 4/2016 | Al-Ali et al. |
| 9,323,894 | B2 | 4/2016 | Kiani |
| D755,392 | S | 5/2016 | Hwang et al. |
| 9,326,712 | B1 | 5/2016 | Kiani |
| 9,333,316 | B2 | 5/2016 | Kiani |
| 9,339,220 | B2 | 5/2016 | Lamego et al. |
| 9,341,565 | B2 | 5/2016 | Lamego et al. |
| 9,351,673 | B2 | 5/2016 | Diab et al. |
| 9,351,675 | B2 | 5/2016 | Al-Ali et al. |
| 9,364,181 | B2 | 6/2016 | Kiani et al. |
| 9,368,671 | B2 | 6/2016 | Wojtczuk et al. |
| 9,370,325 | B2 | 6/2016 | Al-Ali et al. |
| 9,370,326 | B2 | 6/2016 | McHale et al. |
| 9,370,335 | B2 | 6/2016 | Al-ali et al. |
| 9,375,185 | B2 | 6/2016 | Ali et al. |
| 9,386,953 | B2 | 7/2016 | Al-Ali |
| 9,386,961 | B2 | 7/2016 | Al-Ali et al. |
| 9,392,945 | B2 | 7/2016 | Al-Ali et al. |
| 9,397,448 | B2 | 7/2016 | Al-Ali et al. |
| 9,408,542 | B1 | 8/2016 | Kinast et al. |
| 9,436,645 | B2 | 9/2016 | Al-Ali et al. |
| 9,445,759 | B1 | 9/2016 | Lamego et al. |
| 9,466,919 | B2 | 10/2016 | Kiani et al. |
| 9,474,474 | B2 | 10/2016 | Lamego et al. |
| 9,480,422 | B2 | 11/2016 | Al-Ali |
| 9,480,435 | B2 | 11/2016 | Olsen |
| 9,492,110 | B2 | 11/2016 | Al-Ali et al. |
| 9,510,779 | B2 | 12/2016 | Poeze et al. |
| 9,517,024 | B2 | 12/2016 | Kiani et al. |
| 9,532,722 | B2 | 1/2017 | Lamego et al. |

(56) References Cited

U.S. PATENT DOCUMENTS

| | | |
|---|---|---|
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B2 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Schmidt et al. |
| 10,327,713 B2 | 6/2019 | Barker et al. |

(56) References Cited

U.S. PATENT DOCUMENTS

| | | |
|---|---|---|
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,398,320 B2 | 9/2019 | Kiani et al. |
| 10,405,804 B2 | 9/2019 | Al-Ali |
| 10,413,666 B2 | 9/2019 | Al-Ali et al. |
| 10,420,493 B2 | 9/2019 | Al-Ali et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D957,648 S | 7/2022 | Al-Ali |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| 11,464,410 B2 | 10/2022 | Muhsin |
| 11,504,058 B1 | 11/2022 | Sharma et al. |
| 11,504,066 B1 | 11/2022 | Dalvi et al. |
| 2001/0034477 A1 | 10/2001 | Mansfield et al. |
| 2001/0039483 A1 | 11/2001 | Brand et al. |
| 2001/0054161 A1* | 12/2001 | Wooddruff .......... G06F 11/2294 714/27 |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2006/0224107 A1* | 10/2006 | Claus .................. A61F 9/00736 604/521 |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0094228 A1 | 4/2008 | Welch et al. |
| 2008/0202606 A1* | 8/2008 | O'Hara .................. F16K 7/123 137/551 |
| 2008/0221418 A1 | 9/2008 | Al-Ali et al. |
| 2009/0036759 A1 | 2/2009 | Ault et al. |
| 2009/0049522 A1* | 2/2009 | Claus .................... G16Z 99/00 726/4 |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0076453 A1* | 3/2010 | Morris .................. G16H 40/40 606/130 |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2010/0312604 A1* | 12/2010 | Mitchell .......... G06Q 10/06311 705/7.18 |
| 2010/0312605 A1 | 12/2010 | Mitchell et al. |
| 2011/0001605 A1* | 1/2011 | Kiani .................... G16H 40/67 235/492 |
| 2011/0028806 A1 | 2/2011 | Merritt et al. |

(56) References Cited

U.S. PATENT DOCUMENTS

| | | |
|---|---|---|
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0105854 A1 | 5/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0230733 A1 | 9/2011 | Al-Ali |
| 2011/0289363 A1* | 11/2011 | Gadher ............... G06F 11/008 714/E11.202 |
| 2012/0123231 A1 | 5/2012 | O'Reilly |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0135588 A1 | 5/2014 | Al-Ali et al. |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0166182 A1 | 6/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |

(56) References Cited

U.S. PATENT DOCUMENTS

| | | |
|---|---|---|
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0216370 A1 | 8/2018 | Ishiguro et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0038143 A1 | 2/2019 | Al-Ali |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150800 A1 | 5/2019 | Poeze et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216370 A1 | 7/2019 | Schurman et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0254578 A1 | 8/2019 | Lamego |
| 2019/0261857 A1 | 8/2019 | Al-Ali |
| 2019/0269370 A1 | 9/2019 | Al-Ali et al. |
| 2019/0274606 A1 | 9/2019 | Kiani et al. |
| 2019/0274627 A1 | 9/2019 | Al-Ali et al. |
| 2019/0274635 A1 | 9/2019 | Al-Ali et al. |
| 2019/0290136 A1 | 9/2019 | Dalvi et al. |
| 2019/0298270 A1 | 10/2019 | Al-Ali et al. |
| 2019/0304601 A1 | 10/2019 | Sampath et al. |
| 2019/0304605 A1 | 10/2019 | Al-Ali |
| 2019/0307377 A1 | 10/2019 | Perea et al. |
| 2019/0320906 A1 | 10/2019 | Olsen |
| 2019/0320988 A1 | 10/2019 | Ahmed et al. |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |

(56) References Cited

U.S. PATENT DOCUMENTS

| | | |
|---|---|---|
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |

OTHER PUBLICATIONS

International Search Report and Written Opinion for International Application No. PCT/US2014/020795, Notification dated Aug. 21, 2014.

* cited by examiner

SYSTEMS AND METHODS FOR MONITORING A PATIENT HEALTH NETWORK

RELATED APPLICATIONS

This application is a continuation of U.S. patent application Ser. No. 15/948,546, filed on Apr. 9, 2018, and entitled "SYSTEMS AND METHODS FOR MONITORING A PATIENT HEALTH NETWORK," which is a continuation of U.S. patent application Ser. No. 14/198,350, filed on Mar. 5, 2014, and entitled "SYSTEMS AND METHODS FOR MONITORING A PATIENT HEALTH NETWORK," which claims the benefit of priority under 35 U.S.C. § 119(e) of U.S. Provisional Patent Application No. 61/780,794, filed on Mar. 13, 2013, and entitled "SYSTEMS AND METHODS FOR MONITORING A PATIENT HEALTH NETWORK," the disclosures of which are hereby incorporated by reference in their entireties.

BACKGROUND

Field

This disclosure relates to systems, devices, and methods with applications in, for example, hospitals and other patient care facilities. For example, the systems, devices, and methods described herein can be used for monitoring a system that acquires physiological information from patients, analyzes the physiological information, and communicates the physiological information to clinicians and other systems or devices.

Description of the Related Art

Hospitals, nursing homes, and other patient care facilities typically include patient monitoring devices at one or more bedsides in the facility. Patient monitoring devices generally include sensors, processing equipment, and displays for obtaining and analyzing a medical patient's physiological parameters. Physiological parameters include, for example, respiratory rate, $SpO_2$ level, pulse, and blood pressure, among others. Clinicians, including doctors, nurses, and certain other medical personnel use the physiological parameters obtained from the medical patient to diagnose illnesses and to prescribe treatments. Clinicians also use the physiological parameters to monitor a patient during various clinical situations to determine whether to increase the level of medical care given to the patient.

The patient monitoring devices may obtain and analyze a large amount of data (e.g., physiological parameters for one or more medical patients over a long period of time). In addition, the patient monitoring devices may be interconnected via a local network and exchange such data. Clinicians may then have the ability to obtain the physiological parameters even when stationed remotely (e.g., another floor of a hospital, in a building outside a hospital, in a different city, etc.), increasing the quality of medical care provided to patients.

However, the medical care given to patients may be adversely affected if the patient monitoring devices or the systems that support the patient monitoring devices (e.g., a physiological monitoring system) fail (e.g., due to user error, power failure, etc.). While a clinician may detect a failure once it has occurred, the clinician must then identify and notify the appropriate technician. It could take hours to days before a technician can arrive and resolve the issue. Because clinicians and patients may be relying on the physiological parameters to treat ailments, such delay may be unacceptable.

SUMMARY

In order to prevent or reduce the likelihood of a lapse in medical care, it may be beneficial to have the ability to monitor patient monitoring devices or the systems that support the patient monitoring devices. As described above, patient monitoring devices may process and exchange a large amount of data. The processing and exchanging of a large amount of data may cause network communications to become congested (e.g., thereby reducing a data transfer rate and/or preventing data from being transferred), devices to hang, crash, or otherwise become non-responsive, processors to overload (e.g., exceed their processing capabilities), and/or similar ailments. By having the ability to monitor patient monitoring devices or the systems that support the patient monitoring devices, such issues may be identified or predicted to occur. The issues may then be resolved before they result in a lapse in medical care.

As described herein, a system can be constructed to monitor patient monitoring devices or the systems that support the patient monitoring devices, identify issues that are occurring or predict issues that will occur, and resolve such issues. The system may couple to the patient monitoring devices or the systems that support the patient monitoring devices via a network. The system gathers metrics from the patient monitoring devices or the systems that support the patient monitoring devices on a periodic basis. The metrics may be parameters, values, and/or other data that cast a light on the overall health of the patient monitoring devices or the systems that support the patient monitoring devices. For example, the metrics could include processor utilization, memory utilization, network traffic congestion levels, and/or the like. The metrics that can be used by the system are described in greater detail below. Based on an analysis of the metrics, the system determines if there is currently an issue or predicts if an issue will occur with a patient monitoring device or the systems that support the patient monitoring devices. If an issue is identified or predicted, the system may notify the appropriate party (e.g., a clinician, a technician, etc.) so that the issue may be resolved in a timely manner.

Various devices, systems and methods for monitoring physiological monitoring systems are described herein. A method for identifying system performance issue in the physiological monitoring system includes, as implemented by one or more computer systems comprising computer hardware and memory, the one or more computer systems configured with specific executable instructions, receiving, from the physiological monitoring system, first data based on a snapshot taken of a status of the physiological monitoring system at a first time. In an embodiment, the status of the physiological monitoring system comprises at least one indicator of a clinical and/or system performance of the physiological monitoring system. The method can further include comparing, by a processor, the first data with a baseline associated with the physiological monitoring system. The method can further include generating, by the processor, a notification if the first data deviates from the baseline by a predetermined amount. The method can further include transmitting the notification to a system performance monitor.

In certain embodiments, a communication interface module can be configured to receive from a physiological monitoring system first data based on a snapshot taken of a status of the physiological monitoring system at a first time. In an embodiment, the status of the physiological monitoring system comprises at least one indicator of a clinical and/or system performance of the physiological monitoring system. A memory module can be configured to store the first data and a baseline associated with the physiological monitoring system. A processor module can be configured to compare the first data with the baseline associated with the physiological monitoring system and to generate a notification if the first data deviates from the baseline by a predetermined amount. A display module can be configured to display a physical location of a plurality of physiological monitoring systems. In an embodiment, the display module can display the notification and indicate the physiological monitoring system for which the notification is generated.

BRIEF DESCRIPTION OF THE DRAWINGS

Various embodiments will be described hereinafter with reference to the accompanying drawings. These embodiments are illustrated and described by example only, and are not intended to limit the scope of the disclosure.

DETAILED DESCRIPTION

In various embodiments, physiological monitoring systems are systems that monitor one or more parameters of a patient's health. Such systems typically include one or more sensors that measure various physiological signals generated by a medical patient and process the signals to determine any of a variety of physiological parameters. For example, in some cases, a physiological monitoring system can determine any of a variety of physiological parameters of a patient, such as a cardiovascular parameter, a respiratory parameter, an electrical, temperature, chemical, hormonal or other parameter. In some embodiments, the physiological monitoring system monitors a respiratory parameter of the patient, such as: respiratory rate, inspiratory time, expiratory time, i:e ratio (e.g., inspiration-to-expiration ratio), inspiratory flow, expiratory flow, tidal volume, minute volume, apnea duration, breath sounds, rales, rhonchi, stridor, and changes in breath sounds such as decreased volume or change in airflow. In some cases the physiological monitoring system includes an acoustic sensor that detects these or other physiological sounds, such as heart rate, heart sounds (e.g., S1, S2, S3, S4, and murmurs, etc.), changes in heart sounds such as normal to murmur, or split heart sounds indicating fluid overload. The monitoring system can monitor a patient's blood oxygen concentration (e.g., SpO2), or any other blood constituent (e.g., hemoglobin, CO, methemoglobin, etc.). The monitoring system can monitor an electrical parameter of the patient, such as the EKG, EEG, as well. Any of a variety of sensors and monitoring technologies may be included with or provided in communication with such a physiological monitoring system.

A physiological monitoring system of certain embodiments includes one or more patient monitoring devices connected to a shared network using open architecture communications standards. The patient monitoring devices of certain embodiments include a physiological monitor coupled with a network interface module. The physiological monitor includes one or more sensors and a sensor processing module for processing signals from the sensors. The network interface module receives physiological information from the sensor processing module and transmits this information over the shared network. The network interface module may connect to a variety of physiological monitors. In addition, the network interface module of various implementations is a portable bedside device assigned exclusively to one medical patient.

In certain embodiments, the network interface module facilitates establishing a network connection directly with end users over the shared network. These end users, including doctors, nurses, and other hospital staff, may receive physiological information, alarms, and alerts from the network interface module on an electronic device, such as a pager, PDA, laptop, computer, computer on wheels (COW), or the like.

Figure 1:
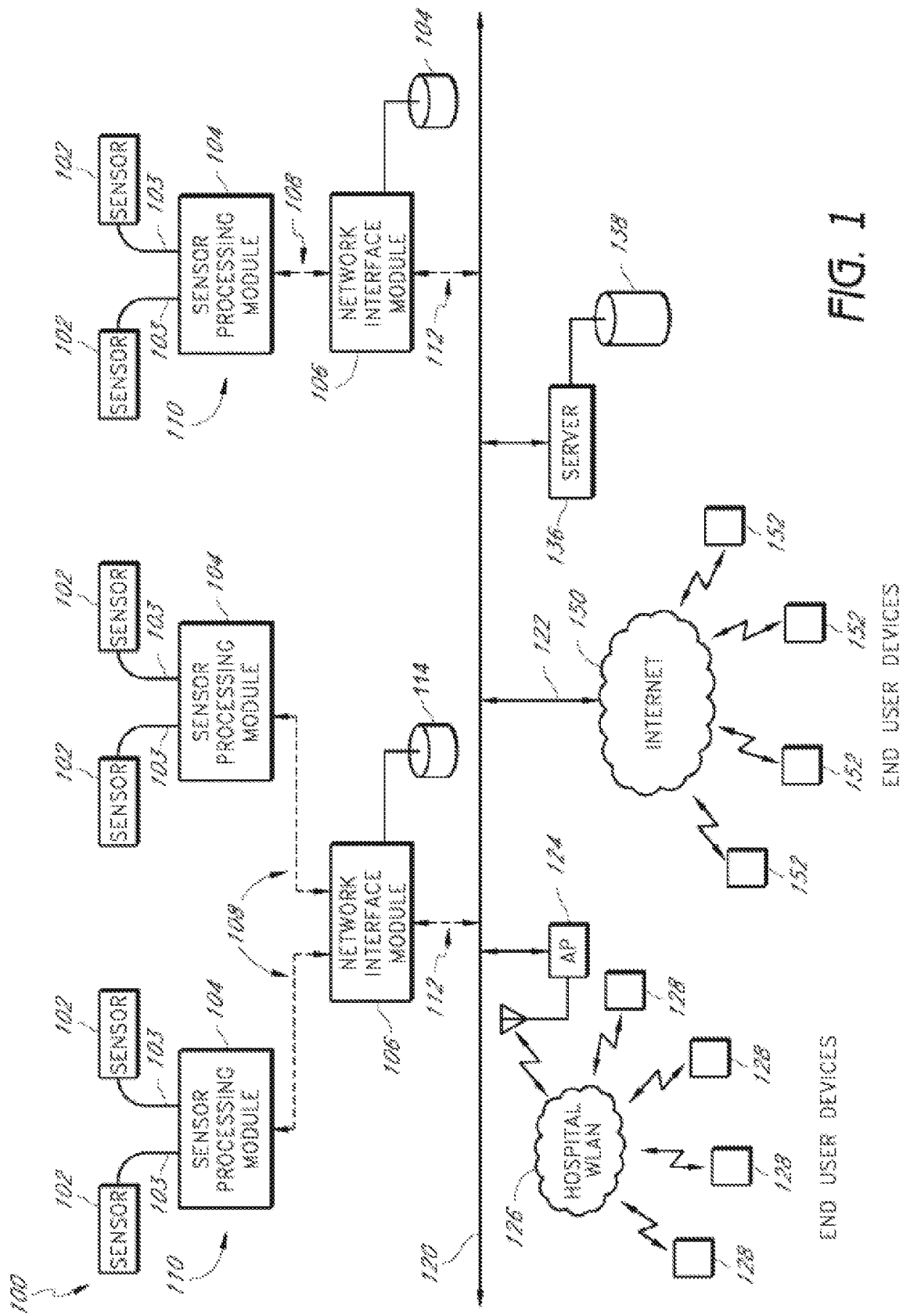
FIG. 1 is an exemplary block diagram showing a physiological monitoring system according to an embodiment of the present invention.

Referring to FIG. 1, certain embodiments of a physiological monitoring system 100 (e.g., alarm notification system) include an open network architecture using "off-the-shelf" hardware and communication protocols. This architecture in various implementations is a shared, or open, network includes multiple patient monitoring devices 110, a network bus 120 (e.g., an Ethernet backbone), and a hospital WLAN 126. In addition, the shared network may further include a connection 122 to an external network, such as the Internet 150, to end user devices 152 over the Internet 150, and to end user devices 128 over the hospital WLAN 126. The physiological monitoring system 100 of certain embodiments is therefore an enterprise system that achieves a cost-effective replacement for currently available patient monitoring systems.

The physiological monitoring system 100 includes a plurality of bedside devices, e.g., patient monitoring devices 110. The patient monitoring devices 110 of various embodiments include sensors 102, one or more sensor processing modules 104, and a communications module, e.g., network interface module 106. In the depicted embodiment, two patient monitoring devices 110 are shown. One patient monitoring device includes one set of sensors 102, one sensor processing module 104, and one network interface module 106. The other patient monitoring device 110 includes two sets of sensors 102, two sensor processing modules 104, and one network interface module 106.

In certain embodiments, each patient monitoring device 110 is used by one medical patient. The patient monitoring devices 110 form a network of patient monitoring devices 110, each of which can communicate with clinicians and other end users over a shared network, including a hospital network 126 and network interfaces to the Internet 150.

One or more sensors 102 of the patient monitoring device 110 are attached to a medical patient. These sensors 102 may include ECG sensors, acoustic sensors, pulse oximeters, and other types of sensors. The sensors 102 obtain physiological information from a medical patient and transmit this information to the sensor processing module 104 through cables 103 or through a wireless connection (not shown). In certain embodiments, the physiological information includes one or more physiological parameters or values and waveforms corresponding to the physiological parameters.

The sensor processing module 104 receives physiological information from the sensors 102. The sensor processing module 104 of certain embodiments includes a circuit having a processor, input ports for receiving the physiological information, software for processing the physiological information in the processor, an optional display, and optionally an input device (e.g., a keyboard). In addition, the sensor processing module 104 contains one or more output ports, such as serial ports. For example, an RS232, RS423, or autobaud RS232 (serial interface standard) port or a universal serial bus (USB) port may be included in the sensor processing module 104.

In certain embodiments, the sensor processing module 104 generates waveforms from signals received from the sensors 102. The sensor processing module 104 may also analyze single or multiparameter trends to provide early warning alerts to clinicians prior to an alarm event. In addition, the sensor processing module 104 in certain embodiments generates alarms in response to physiological parameters exceeding certain safe thresholds.

Example alerts include no communication with pulse oximeter, alarm silenced on pulse oximeter, instrument low battery (pulse oximeter), and transmitter low battery. Example alarms include $SpO_2$ levels and alarms, high and low $SpO_2$, high and low PR, HbCO level and alarms, HbMET level and alarms, pulse rate and alarms, no sensor, sensor off patient, sensor error, low perfusion index, low signal quality, HbCO, HbMET, PI trend alarm, and desat index alarm.

The network interface module 106 in the depicted embodiment is connected to one or more sensor processing modules 104 through one or more connectors 108, which may be serial connectors corresponding to the serial ports in the sensor processing modules 104. Dashed lines on the connector 108 indicate that the network interface module 106 of certain embodiments is not permanently attached to the sensor processing modules 104. In alternative embodiments (not shown), however, the network interface module 106 is contained within a sensor processing module 104.

The network interface module 106 in various implementations includes a processor, an input port (such as a standard RS232 serial port), a network output port such as an Ethernet port, and software which enables the network interface module 106 to act as a network-communications enabled device. In addition, the network interface module 106 includes a storage device 114, which may be included within the network interface module 106 or attached separately to the network interface module 106.

The network interface module 106 manages the connectivity overhead for initiating and maintain connectivity with end user devices over the shared network. In certain embodiments, the network interface module 106 manages connectivity by acting as a microserver or web server. In such instances, the network interface module 106 is a network connection enabled device. As a web server, the network interface module 106 establishes direct connections to the Internet 150, such that an end user may access web pages stored on the storage device 114 of the network interface module 106. In one embodiment, the network interface module 106 therefore does not require a separate server for connecting to the Internet 150. In one embodiment, the network interface module 106 connects to the Internet 150 directly through a modem, such that the connection 122 includes a modem. In managing connectivity over the shared network, the network interface module 106 may also perform security management functions, such as user authentication.

In certain embodiments, the network interface module 106 sends data over the shared network through an access point 124 or other wireless or wired transmitter. Alternatively, the network interface module 106 may communicate physiological information directly to end users over the Internet 150. End users such as clinicians carrying notifier devices, e.g., end user devices 128, 152 connected to the hospital WLAN 126 may receive real-time viewing of physiological patient parameters and waveforms on demand or in the event of an alarm or alert. Real-time or slightly delayed transmission of physiological information in certain embodiments comports with standards for alarm latency in compliance with Joint Commission on Accreditation of Healthcare Organizations (JCAHO) standards for effective alarm response. The network interface module 106 of certain embodiments therefore adds functionality equivalent to a central nurses' station.

In certain embodiments, the network interface module 106 performs context management. In one embodiment, context management includes associating context information with physiological information to form a contextual data package. Context information may include several categories of information, including the categories of context information related to the network interface module 106, context information related to the medical patient, context information related to usage of the network interface module 106, and context information related to a network connection. Within one or more of these context categories, context information might include a patient name, a patients' unique hospital identification number, patient location, an identification number for a network interface module 106, time stamps for events occurring in the physiological monitoring system 100, environmental conditions such as changes to the state of the network and usage statistics of the network interface module 106, and identification information corresponding to the network link (e.g., whether the network connection is WiFi or Ethernet). In one embodiment, the context information in the contextual data package may include all of or any subset of context information from one or more of the context categories.

The network interface module 106 receives context information, for example, by a nurse entering the information in the network interface module 106 or from a server 136. In one embodiment, by receiving this information (including, e.g., patient identification number and location), the network interface module 106 becomes exclusively assigned to the medical patient. The network interface module 106 transmits or communicates the contextual data package to clinicians during an alarm or alert, upon clinician request, or on a scheduled basis. In addition, the network interface module 106 may transmit a continuous stream of physiological information to clinicians.

By optionally connecting to multiple sensor processing modules 104 in certain embodiments, the network interface module 106 is able to associate patient context information and other context information with multiple sensor processing modules 104. Consequently, context can be created for one or more sensor processing modules 104 in addition to context being created for the network interface module 106.

In addition to transmitting the contextual data package, the network interface module 106 in one embodiment stores the contextual data package in the storage device 114. The storage device 114 may be a flash memory, a hard disk drive, or other form of non-volatile or volatile memory. In certain embodiments the storage device 114 acts as a flow control buffer. The network interface module 106 uses the storage device 114 acting as a flow control buffer to perform flow control during communications.

In some implementations, a server 136 may optionally be included in the physiological monitoring system 100. The server 136 in these implementations is generally a computing device such as a blade server or the like. In certain embodiments, the server 136 is an appliance server housed in a data closet. In other embodiments, the server 136 is a server located at a central nurses' station, such as a workstation server.

The server 136 receives contextual data packages from a plurality of network interface modules 106 and stores the contextual data package in a storage device 138. In certain embodiments, this storage device 138 therefore archives long-term patient data. This patient data may be maintained even after the patient is discharged. In storing patient data, the server 136 may act as an interface between the shared network and an external electronic medical record (EMR) system.

The server 136 may also store data concerning user interactions with the system and system performance metrics. Integrated into the server 136 of certain embodiments is a journal database that stores every alert and alarm or a subset of the alerts and alarms as well as human interaction in much the same way as an aviation "black box" records cockpit activity. The journal is not normally accessible to the clinical end user and, without technical authorization, cannot be tampered with. In addition, the server 136 may perform internal journaling of system performance metrics such as overall system uptime.

In one embodiment, the journaling function of the server 136 constitutes a transaction-based architecture. Certain transactions of the physiological monitoring system 100 are journaled such that a timeline of recorded events may later be re-constructed to evaluate the quality of healthcare given and/or to evaluate the performance of the physiological monitoring system 100. These transactions include state changes relating to physiological information from the patient monitoring devices 100, to the patient monitoring devices 110, to the hospital WLAN 126 connection, to user operation, and to system behavior. Journaling related to the physiological information received from a physiological monitor in one embodiment includes recording the physiological information itself, recording changes in the physiological information, or both.

The server 136 in certain embodiments provides logic and management tools to maintain connectivity between network interface modules 106, clinician notification devices such as PDAs and pagers, and external systems such as EMRs. The server 136 of certain embodiments also provides a web based interface to allow installation (provisioning) of software rated to the physiological monitoring system 100, adding new devices to the system, assigning notifiers (e.g., PDAs, pagers, and the like) to individual clinicians for alarm notification at beginning and end of shift, escalation algorithms in cases where a primary caregiver does not respond to an alarm, interfaces to provide management reporting on the alarm occurrence and response time, location management, and internal journaling of system performance metrics such as overall system uptime (see, e.g., FIG. 3 and accompanying description).

The server 136 in certain embodiments also provides a platform for advanced rules engines and signal processing algorithms that provide early alerts in anticipation of a clinical alarm. The operating system on the server 136 in one embodiment is Linux-based for cost reasons, though a Microsoft-based or other operating system may also be used. Moreover, the server 136 is expandable to include data storage devices and system redundancy capabilities such as RAID (random array of independent disks) and High Availability options.

In another embodiment (not shown), end user devices 128, 152 include one way POCSAG Pagers having a 2 line display with audible and vibrate mode, of suitable size and durability for severe mechanical environments typical of hospital general floor settings. In yet another embodiment, the end user devices 128, 152 include two way paging systems, such as Motorola Flex and WLAN pagers. One advantage of two-way paging is the ability to confirm message receipt and the ability to remotely silence alarms. Wireless PDAs may also be used by end users based on ruggedness and acceptable form factors as determined by an end user. An example of such a device is the Symbol Technology MC50 PDA/Barcode Scanner.

Figure 2:
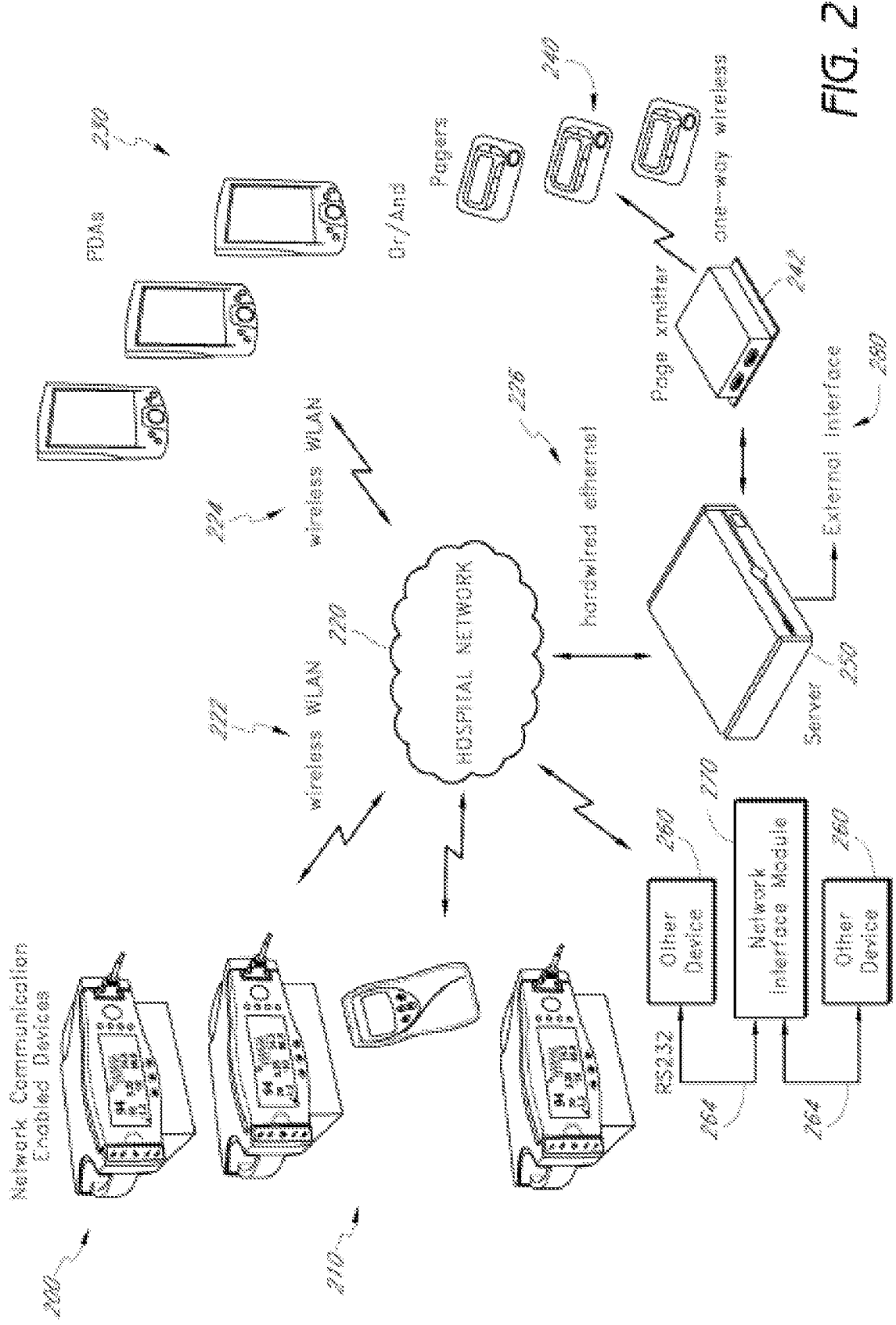
FIG. 2 is an exemplary block diagram showing another embodiment of a physiological monitoring system.

FIG. 2 depicts another embodiment of the physiological monitoring system 200 of the present invention. The physiological monitoring system 200 includes network communications enabled devices 210. The network communications enabled devices 210 are connected directly to a hospital network 220 through a wireless connection. In certain embodiments, the network communications enabled devices 210 include sensors and sensor processing modules, similar to the sensors 102 and sensor processing modules 104 of FIG. 1. Certain of these network communications enabled devices 210 are bedside devices, and others are handheld or otherwise patient-worn devices that may be used by an ambulatory (mobile) patient.

The hospital network 220 transmits physiological information and context information to clinician notifier devices, including pagers 240, PDAs 230, and the like. In certain embodiments, the hospital network 220 utilizes a server 250 to transmit contextual data packages to a page transmitter 242, which further transmits the data to one-way wireless pagers 240. An external interface 280 may be coupled with the server 250. The external interface 280 could include one or more of the following: enterprise paging, nurse call systems, wide area paging systems, enterprise clinical and patient information systems, and third party monitoring and surveillance systems.

Certain other devices 260, such as some patient monitoring equipment, are not network communications enabled devices. That is, these other devices 260 are unable to connect to a network unaided. In the depicted physiological monitoring system 200, example devices 260 that are not network communications enabled are connected to a network interface module 270. The network interface module 270 is connected to the non-network communication enabled other devices 260 through RS232 cables 264. Such a connection is a standardized serial connection found on many devices. Because the network interface module 270 has an RS232 port, the network interface module 270 can allow non-network communication enabled patient monitoring devices to connect directly to the hospital network 220 and also to the Internet.

Moreover, by connecting to one or more other devices 260 in some embodiments, the network interface module 270 is able to associate patient context information and other context information with one or more other devices 260. Consequently, context can be created for one or more other devices 260 in addition to context being created for the network interface module 270.

Figure 3:
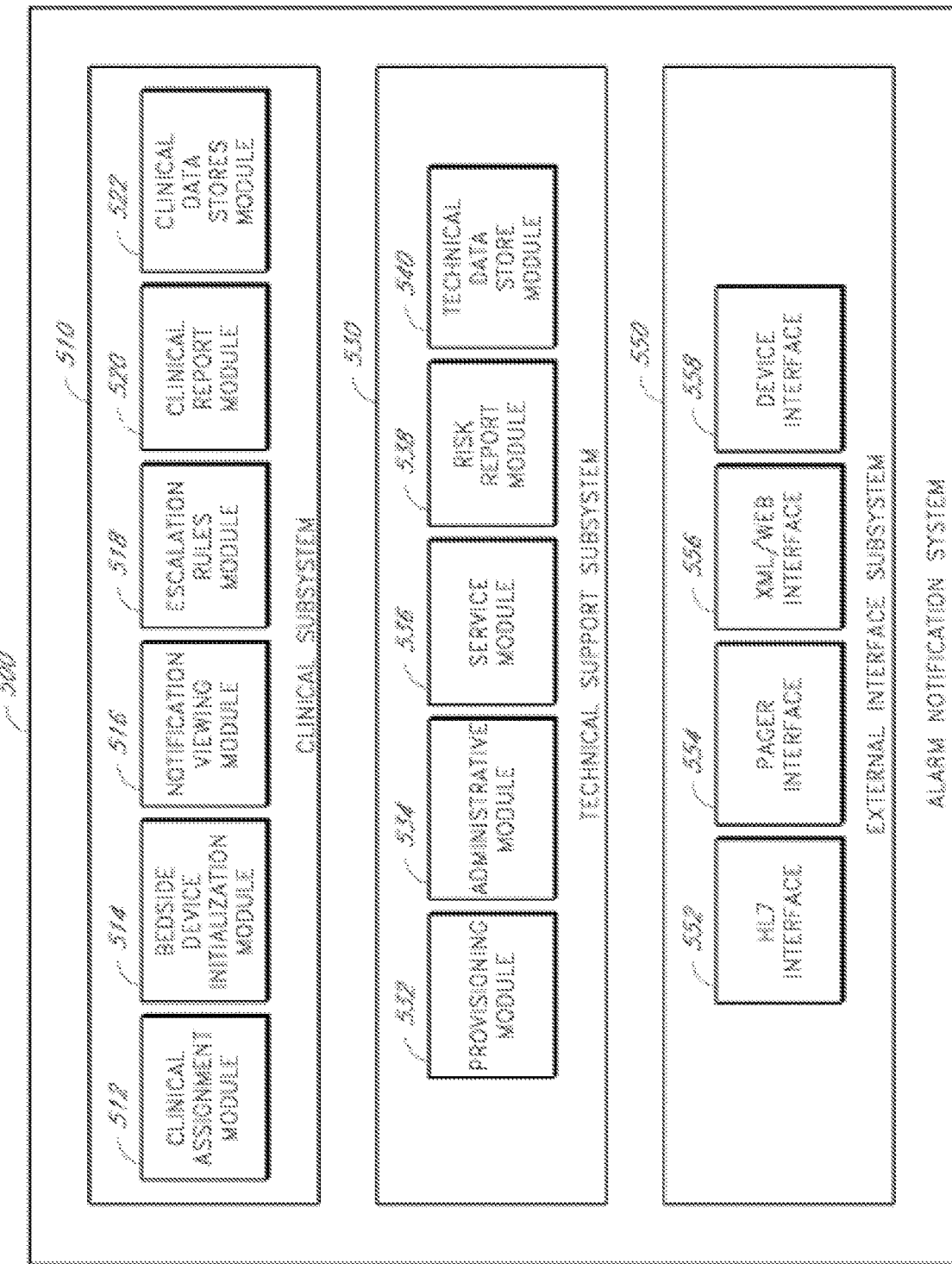
FIG. 3 is an exemplary block diagram showing an alarm notification system according to an embodiment of the present invention.

FIG. 3 depicts an alarm notification system 500 in accordance with certain embodiments of the present invention. A clinical subsystem 510 defines the major software components of alarm notification system 500 including a clinical assignment module 512, a bedside device initialization module 514, a notification and viewing module 516, an escalation rules module 518, a clinical report module 520, and a clinical data stores module 522. An authentication feature is built into mobile computing devices in compliance with HIPAA and hospital IT policies.

The clinical assignment module 512 has an assignment function. A nursing supervisor assigns individual nurses to specific patients at the start of each shift and upon admission of new patients. Shift assignments take place at change of shift during a "report" transition exercise where individual nurses and nursing supervisor from previous shift "hand off" patients to the next shift. The report can be either formal where all nurses attend or informal dependent on hospital nursing service policies and procedures. The clinical assignment module 512 provides an intuitive interface that allows a listing of available nurses to be assigned individual patients. The major user of this module is the unit clerk as assigned by the nursing supervisor. A nurse can be assigned one or more patients or all patients. An alternative work flow is self assignment where individual nurses assign patients themselves in which case they perform functions of the unit clerk. In the self assignment model, a default is implemented where any unassigned patient is either assigned to all nurses or the nursing supervisor.

The bedside device initialization module 514 has bedside devices, such as the network interface modules described above, that are sometimes set up by an aide to the nurse. In the case where the nurse performs this task, she or he performs the functions of the nursing aide. Work flow includes delivering a device to bedside, applying sensors, initializing the device, and setting patient context, such as name, ID and location.

The notification and viewing module 516 assigns a wireless notification device, such as a one-way pager, PDA, IP telephone, COW, or Tablet to individual nurses. The device becomes associated with her or him. Alarms are routed to the notification device based on the clinical assignment module 512. Non-dedicated notifier solutions such as hospital owned paging systems issued to nurses have unknown latency characteristics. A general purpose interface is available at the server with a latency of less than 1 second upon receipt from the bedside device and is time stamped upon presentation to the server external interface and stored in a journaling system within the server. An additional interface for mobile computing platforms such as PDA, COWS, and Tablets allows viewing of current and trend data for an individual patient.

The escalation rules module 518 has a rules engine that actuates an escalation policy defined by the hospital. The escalation rules module 518 provides alternative routing of alarms to alternative and additional clinical users in the event an alarm is not responded to or persists for a predefined (e.g., by a policy) period of time. The escalation rules module 518 in certain embodiments routes alarms to an emergency response team.

The clinical report module 520 provides predefined formatted reports on the clinical data from which to determine physiologic condition and/or progress. More than one report may be dependent on end user needs. Reports are not time critical views of individual patients and may be remotely viewed by clinicians who have alarm notification system 500 privileges and have been authenticated by the alarm notification system 500. These reports are web browser views that allow clinicians to set viewing parameters such as time and parameter scales and alarm review.

The clinical data stores module 522 provides data storage and database resources to store information as known to those skilled in the art.

Further shown in FIG. 3, a technical support subsystem 530 is isolated from the clinical subsystem 510 in compliance with HIPAA and as such does not allow viewing or access to any patient information with the exception of the risk report module 538. The technical support subsystem 530 includes a provisioning module 532, an administration module, a service module 536, a risk report module 538, and a technical data store module 540.

The provisioning module 532 provides provisioning, which is the initial installation of the system and first customer use. The primary user of the provisioning module 532 is the field installer. The provisioning module 532 contains all the start up scripts and system configurations to bring the system from shipping boxes to full alarm notification system 500 functionality. Provisioning includes steps to configure individual devices, notifiers such as pagers, PDA, COW, Tables and IP telephone at the customer site, preferably by wireless means (e.g., Bluetooth).

The administrative module 534 provides a system interface for the application administrator to set up users, set policies for various actor privileges such as a nurse's aide being able to set or change alarms, set up allowed device connection identifications, and other general systems administrative duties typical of IT systems.

The service module 536 provides interfaces for various technical support actors including remote service, IT Service, and Biomed Service. Each of these actors may perform each other's functions. Interfaces allow the service actors to access system performance data to access performance, for example, data traffic, device assets connected, software version management, CPU loading, network loading, etc. and execute remote technical service procedures, for example, resetting a printer queue, repartition of disk, uploading software patches, etc. The service module 536 includes a full journaling function that stores every user interaction or a portion of user actions that can be captured by the system, especially changes in default values or alarm settings.

The risk report module 538 provides summary reports on alarm occurrences, duration of alarm, clinical response time to alarms and other statistical data to determine overall effectiveness of clinical response to alarms in compliance with JCAHO, other regulatory bodies, and internal quality assurance committees.

The technical data stores module 540 has the same characteristics as the clinical data stores module 522 except that the technical data stores module 540 is used for technical data. The technical data stores module 540 may or may not share the same physical and logical entity as the clinical data stores module 522.

Additionally shown in FIG. 3, an external interface subsystem 550 provides interfaces to bedside devices and external systems such as electronic medical records, admit discharge, transfer systems, POCSAG pager systems, middleware engines such as Emergin, and Web/XML enabled devices such as wireless PDAs, COWs and Tablet PCs. The external interface subsystem 550 has an HL7 interface 552, a pager interface 554, an XML/Web interface 556, and a device interface 558.

The HL7 interface 552 provides a bi-directional interface to electronic medical records (EMR) and supports both push and pull models. The push model is when a bedside nurse initiates data transfer. The pull model is when an EMR system polls the alarm notification system 500 server. The pager interface 554 provides output to external paging system. Message latency is identified to an end user for any user-owned paging solution. This same output can be used for middleware alarm notification systems such as Emergin. The XML/Web interface 556 provides bi-directional interface with mobile computing platforms such as wireless PDA, COWs, Tables, and Web-enabled IP phones. Mobile computing platforms support Web Browser XML applications. The device interface 558 provides a bi-directional interface to bedside devices as well as to other devices enabled by the communications module or accessory. Application Programmer Interface (API) capability is an option for interfacing to other bedside devices.

The major end users of the alarm notification system 500 system (not shown or described for simplicity) include hospital electronic medical records, admit discharge transfer, pharmacy, clinical information, patient flow tracking and others. Actors, e.g., users of the alarm notification system 500, including clinical actors and technical support actors. The clinical actors include nursing supervisors, unit clerks, nursing aides, nurses, rapid response teams and respiratory therapists.

A nursing supervisor assigns individual nurses to specific patients at the beginning of each shift. Shift can vary according to hospital staffing policies. A unit clerk takes direction from the nursing supervisor, typically inputs assignments into system and monitors overall system. A unit clerk may not be available for all shifts. A nursing aide takes assignments from nurse or nursing supervisor, typically applies bedside device sensor, initializes the bedside device and sets alarms to default values. A nurse has primary responsibility for individual patient care and primary response to alarms. The nurse is assigned by nursing supervisor to more than one patient dependent on her/his skills and patient needs and is not always assigned the same patient. Nursing aides are not found in all hospitals.

A rapid response team responds to clinical emergencies initiated by either a bedside nurse or a nursing supervisor. The team supports more than one care unit and has one or more members depending on shift. Rapid Response Teams may not be implemented in all hospitals. A respiratory therapist has responsibilities for management of respiratory care for more than one patient and usually more than one care unit. Respiratory therapists are not found in some international settings.

Clinical actor performance substitution allows a high capability actor to assume the roles of other actors. Alarm notification system 500 allows mechanisms for such performance. For example, a nursing supervisor may perform functions of a unit clerk nursing aide, a nurse and a rapid response team. A nurse may perform functions of a unit clerk, a nursing aide and a rapid response team. In some international markets a nurse may perform the functions of a respiratory therapist.

The technical support actors include field installers, application administrators, remote services, IT engineers, biomedical engineers and risk managers. A field installer provisions the system for initial installation, installs components, and validates that the installation and configuration meet a purchasing contract. An application administrator sets up and maintains user accounts and systems defaults. A remote service provides remote diagnostics and system maintenance over a remote link, such as dial up and VPN. An IT engineer provides network support services if the system is integrated with the hospital IT network. A biomedical engineer provides bedside and system primary service. A risk manager reviews reports for quality and risk mitigation purposes. Technical support actors may also fill in for other actors. For example, an IT engineer, a biomedical engineer, or a remote service can perform the functions of an application administrator. An IT engineer or a biomedical engineer can perform each other's functions.

In certain embodiments, systems and methods are provided for rapidly storing and acquiring physiological trend data. For instance, physiological information obtained from a medical patient can be stored in a round-robin database. The round-robin database can store the physiological information in a series of records equally spaced in time. Parameter descriptors may be used to identify parameter values in the records. The parameter values can be dynamically updated by changing the parameter descriptors to provide for a flexible database. In addition, the size of files used in the database can be dynamically adjusted to account for patient condition.

Additionally, in certain embodiments, medical data obtained from a clinical network of physiological monitors can be stored or journaled in a journal database. The medical data can include device events that occurred in response to clinician interactions with one or more medical devices. The medical event data may also include device-initiated events, such as alarms and the like. The medical data stored in the journal database can be analyzed to derive statistics or metrics, which may be used to improve clinician and/or hospital performance.

Figure 4:
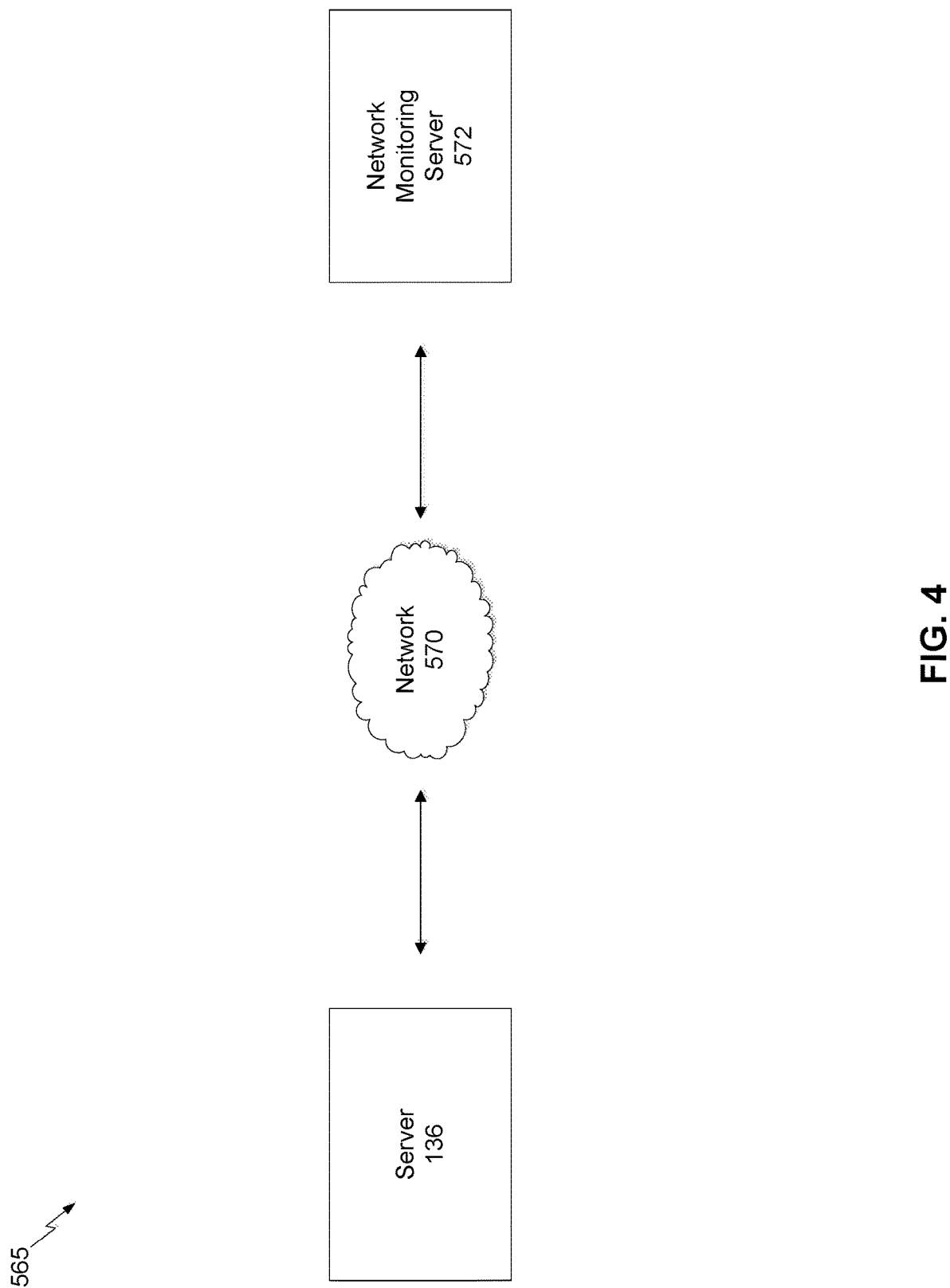
FIG. 4 is a block diagram of a system that may monitor a physiological monitoring system, such as the physiological monitoring system of FIG. 1.

FIG. 4 depicts a block diagram of a system 565 that may monitor a physiological monitoring system, such as the physiological monitoring system 100 described herein with respect to FIG. 1. In certain embodiments, the system 565 comprises a server of the physiological monitoring system 100, such as server 136 described herein with respect to FIG. 1, a network 570, and/or a network monitoring server 572. While FIG. 4 illustrates one network monitoring server 572, this is not meant to be limiting, as the functionality described herein may be implemented in more than one server (e.g., these servers can be co-located or can be geographically separate, etc.). The functionality described herein may also be implemented in one or more virtual machines that execute on a physical server. In addition, the functionality described herein may be implemented in network monitoring server 572 or in other computing devices. Further, the functionality described herein may be implemented in a cloud computing environment.

As described herein, the server 136 may store data concerning user interactions with the system (e.g., clinical performance metrics, such as number of alarms, alarm response times, etc.) and system performance metrics. In certain embodiments, certain transactions of the physiological monitoring system 100 are journaled by the server 136 such that a timeline of recorded events may later be reconstructed to evaluate the quality of healthcare given and/or to evaluate the performance of the physiological monitoring system 100. For example, the server 136 may capture the data concerning user interactions with the system and system performance metrics by taking a snapshot of the physiological monitoring system 100 (e.g., a state of the physiological monitoring system) at a given point in time. The server 136 may capture such data by requesting reports, logs, or the like from various modules within the physiological monitoring system 100 (e.g., the service module 536, the risk report module 538, etc.). The server 136 may also transmit the data concerning user interactions with the system and system performance metrics to the network monitoring server 572 via the network 570. In an embodiment, the server 136 may capture and/or transmit the data in regular intervals, such as every minute, every hour, every day, and/or the like.

The network 570 may include any communications network, such as the Internet 150. Network 570 may be a wired network, a wireless network, or a combination of the two. For example, the network 570 may be a local area network (LAN), a wide area network (WAN), the Internet, and/or combinations of the same.

The network monitoring server 572 may be in communication with any of a variety of information-providing devices, either directly or via the network 570. For example, the network monitoring server 572 may be in communication with one or more servers associated with one or more physiological monitoring systems. In certain embodiments, the network monitoring server 572 may be configured to receive data concerning user interactions with the system and system performance metrics from each physiological monitoring system that it is in communication with. The network monitoring system 572 may also be configured to generate and transmit messages, such as notifications, commands, and/or instructions, to each physiological monitoring system that it is in communication with. In this way, the network monitoring server 572 may be able to identify current and/or future clinical and/or system performance issues and respond appropriately.

Figure 5:
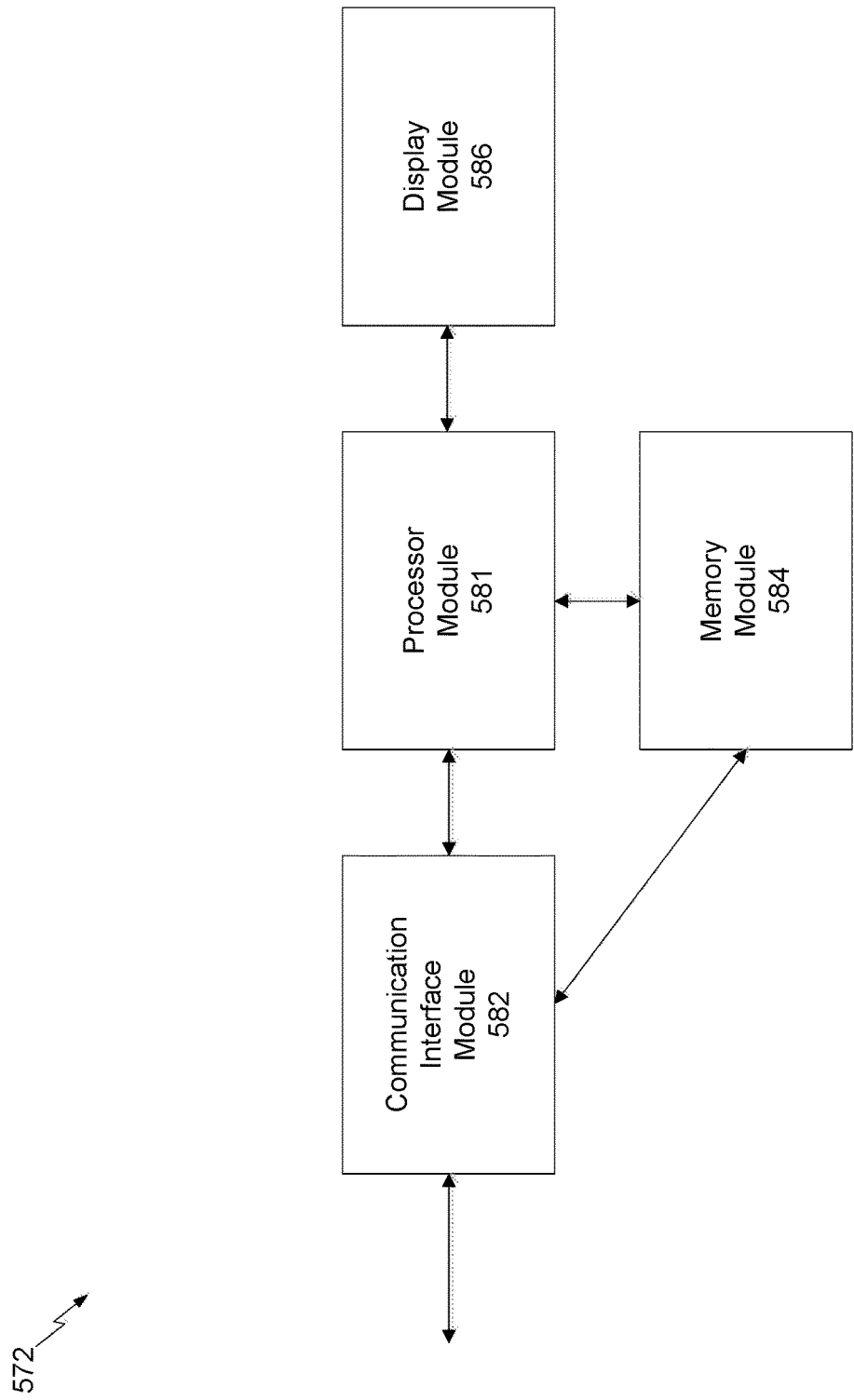
FIG. 5 is a more detailed block diagram of a network monitoring server, such as the network monitoring server of FIG. 4.

FIG. 5 illustrates a more detailed block diagram of a network monitoring server, such as network monitoring server 572 described herein with respect to FIG. 4. The network monitoring server 572 may comprise a communication interface module 582, a processor module 581, a memory module 584, and/or a display module 586.

In certain embodiments, the communication interface module 582 is configured to communicate with the servers associated with physiological monitoring systems, such as server 136. For example, the communication interface module 582 may receive data, such as clinical and/or system performance metrics, from the server 136. The communication interface module 582 may receive the clinical and/or system performance metrics from the server 136 in regular intervals or when such metrics deviate from a baseline (e.g., historical values) as described herein. As an example, clinical and/or system performance metrics may include indicators of clinical and/or system performance, such as processor utilization by the physiological monitoring system 100, memory utilization by the physiological monitoring system 100, a number of times a subsystem (e.g., the clinical subsystem 510, the technical support subsystem 530, and/or the external interface subsystem 550 of the alarm notification system 500) associated with the physiological monitoring system 100 failed, a number of times at least one medical device (e.g., sensor 102, sensor processing module 104, network interface module 106, end user devices 128, end user devices 152, other devices like radios, cameras, or the like, etc.) disconnected from the physiological monitoring system 100, a number of times at least one medical device generated an alarm condition (e.g., when an alarm occurs), a number of errors (e.g., login/credential errors, system driver errors, software errors, etc.) generated by the physiological monitoring system 100, a number of times at least one medical device generated an alarm condition that lasted more than a predetermined amount of time (e.g., several seconds, like three or four, which may indicate that a page was sent to an end user device 128 and/or 152), and a number of times at least one medical device generated an alarm condition that lasted less than the predetermined amount of time (e.g., which may indicate that a page was not sent to an end user device 128 and/or 152). If applicable, the communication interface module 582 may be further configured to receive information identifying and otherwise relating to the medical device(s) and/or other component(s) of the physiological monitoring system 100 that may be causing clinical and/or system performance issues.

The received clinical and/or system performance metrics may be stored in the memory module 584. In certain embodiments, the received data may be aggregated for use by the processor module 581 as described herein. In further embodiments, the memory module 584 may store baseline information associated with each physiological monitoring system that the network monitoring server 572 is in communication with. For example, at or near a first time when the physiological monitoring system and the network monitoring server 572 are in communication, the network monitoring server 572 may receive the clinical and/or system performance metrics from the physiological monitoring system for storage in the memory module 584. After a set number of data points (e.g., data communication sessions between the network monitoring server 572 and the physiological monitoring system occurring at different times) have been received (e.g., 5 data points, 10 data points, etc.), such data points may be aggregated and identified as the baseline clinical and/or system performance metrics associated with the respective physiological monitoring system. This baseline information may represent the clinical and/or system performance metrics that are to be considered normal for the respective physiological monitoring system. Any deviation from this baseline may indicate that there is some issue that is or will be occurring in the respective physiological monitoring system. In other words, identifying any deviation from this baseline may allow the network monitoring server 572 to identify an issue that is occurring or predict an issue that could occur in the future.

In certain embodiments, aggregation may occur by clinical and/or system performance indicators. For example, metrics related to a number of times at least one medical device generated an alarm condition that lasted more than a predetermined amount of time may be aggregated together, metrics related to a number of times at least one medical device generated an alarm condition that lasted less than the predetermined amount of time may be aggregated together, and so on. In further embodiments, aggregation may occur by physiological monitoring system such that metrics from different physiological monitoring systems would not be aggregated together. Each of the metrics may retain their identifying information (e.g., the physiological monitoring system the metric is associated with, a time the metric was captured at the physiological monitoring system, etc.) when aggregated such that aggregated data may yield trends and/or other information if plotted or otherwise visually displayed.

The processor module 581 may be configured to retrieve data from the communication interface module 582 and/or the memory module 584. For example, the processor module 581 may be configured to retrieve clinical and/or system performance metrics from the communication interface module 582 and/or the memory module 584 and/or aggregated data from the memory module 584. The processor module 581 may also be configured to generate baseline information as described herein, and store and retrieve baseline information from the memory module 584. In certain embodiments, the processor module 581 compares a single set of clinical and/or system performance metrics and/or the aggregated data with the baseline information to determine whether there is any deviation from the baseline. Thus, the processor module 581 is configured to determine whether an issue is occurring and/or predict whether an issue will occur in the future based on the comparison.

As described herein, a deviation from the baseline may indicate there is an issue with the clinical and/or system performance within the physiological monitoring system 100. For example, if the baseline information indicates that a normal number of errors generated by the physiological monitoring system 100 during a given period (e.g., an hour, a day, a week, etc.) is 20, then there is or there may be an issue with the clinical and/or system performance within the physiological monitoring system 100 if the aggregated data and/or the received single set of clinical and/or system performance metrics indicates that a number of errors generated by the physiological monitoring system 100 during the same given period deviates from 20 by a predetermined amount (e.g., deviates by a certain percentage, deviates by certain number, etc.).

In certain embodiments, if the processor module 581 determines that there is sufficient deviation from the baseline, the processor module 581 may generate a notification. The processor module 581 can generate the notification at a time or near a time that there is sufficient deviation from the baseline. Alternatively or in addition, the processor module 581 can generate the notification at the end of a periodic interval. The notification may be displayed (e.g., via the display module 586) and/or transmitted to a system performance monitor (e.g., a computing device within the physiological monitoring system 100, an entity that monitors the physiological monitoring system 100, such as the user of the network monitoring server 572, a computing device outside the physiological monitoring system 100, a paging service, a database, etc.) via the communication interface module 582. As an example, a notification may inform a user of the network monitoring server 572 and/or operators of the physiological monitoring system 100 of a medical device(s) and/or other component(s) of the physiological monitoring system 100 that may be causing problems to the system (e.g., that caused the generation of the notification). The notification may also include a command or instructions on how to solve the current or potential issue. In some aspects, such a command or instruction may explain to a user how to solve the current or potential issue. In other aspects, such a command or instruction is executed by a processor or other such device within the physiological monitoring system 100 or the network monitoring server 572 to solve the current or potential (e.g., predicted) issue. For example, the service module 536 may execute such a command or instruction.

The display module 586 may be a display, such as a screen (e.g., an LCD screen, an LED screen, a touch screen, etc.). In some aspects, the display module 586 may receive inputs, such as touch inputs, from a user. The display module 586 may be configured to display a geographic region and the locations of one or more physiological monitoring systems within the geographic region. The one or more physiological monitoring systems may be represented using any symbol. As described herein, the display module 586 may further be configured to display the notification. For example, when a notification is generated, the display module 586 may display the notification (immediately or after the physiological monitoring system it is associated with is chosen) and/or the physiological monitoring system it is associated with.

In certain embodiments, the physiological monitoring system may be indicated graphically (e.g., via a different color symbol, a flashing symbol, text, etc.) and/or may be selectable by a user. Upon selecting a physiological monitoring system (e.g., by touching, clicking, pressing, hovering over, typing, speaking, etc.), further information may be displayed, such as a single set of clinical and/or system performance metrics and/or aggregated data. In this way, a user associated with the network monitoring server 572 may be able to access and view clinical and system performance metrics for a selected physiological monitoring system. The user may be able to view such metrics to further investigate current and/or potential issues with the physiological monitoring system and/or to identify issues with the physiological monitoring system even if no notification has been generated.

Figure 6A:
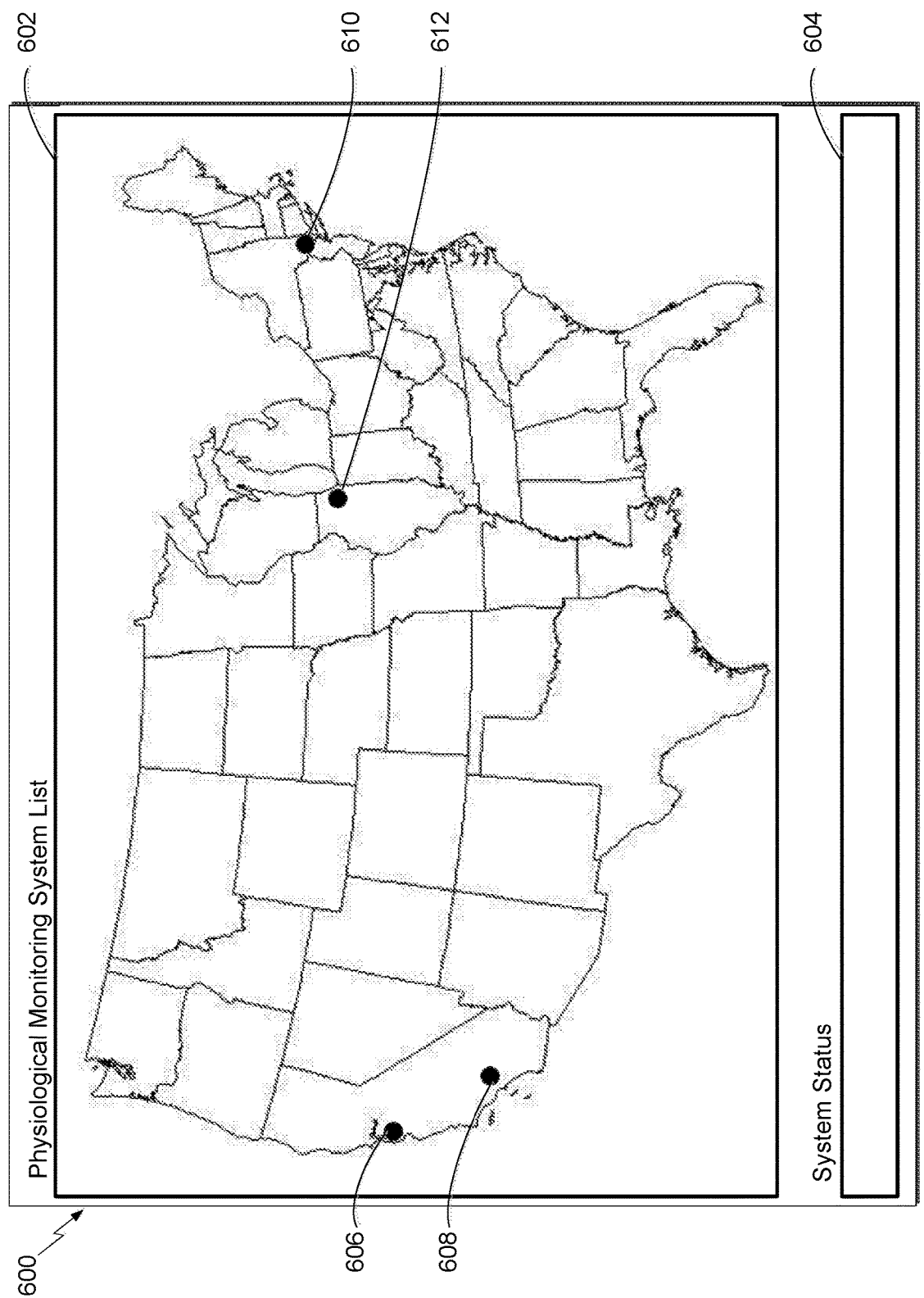
FIGS. 6A-C are a network monitoring screen that may be generated by a display module, such as the display module of FIG. 5.
Figure 6B:
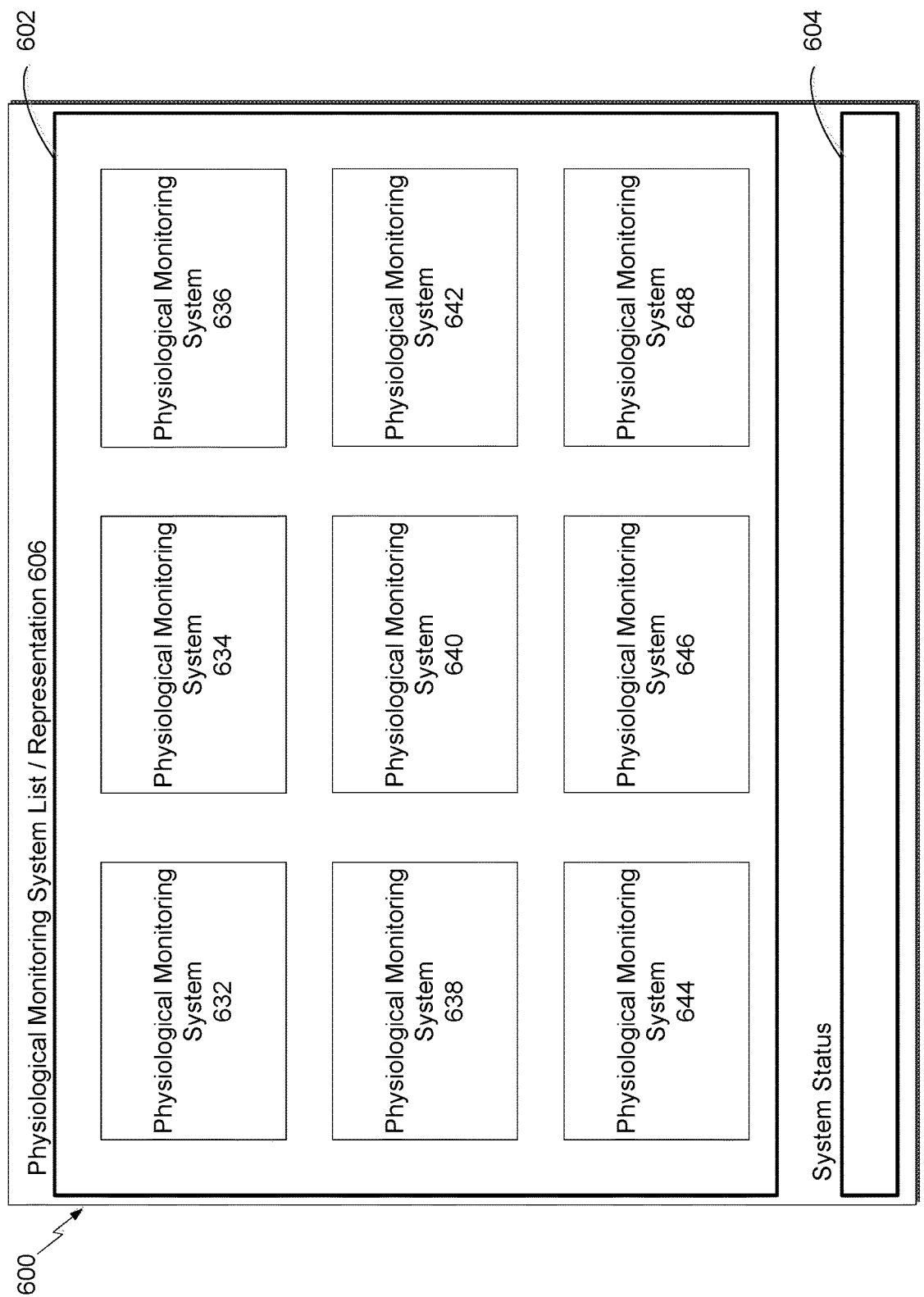
Figure 6C:
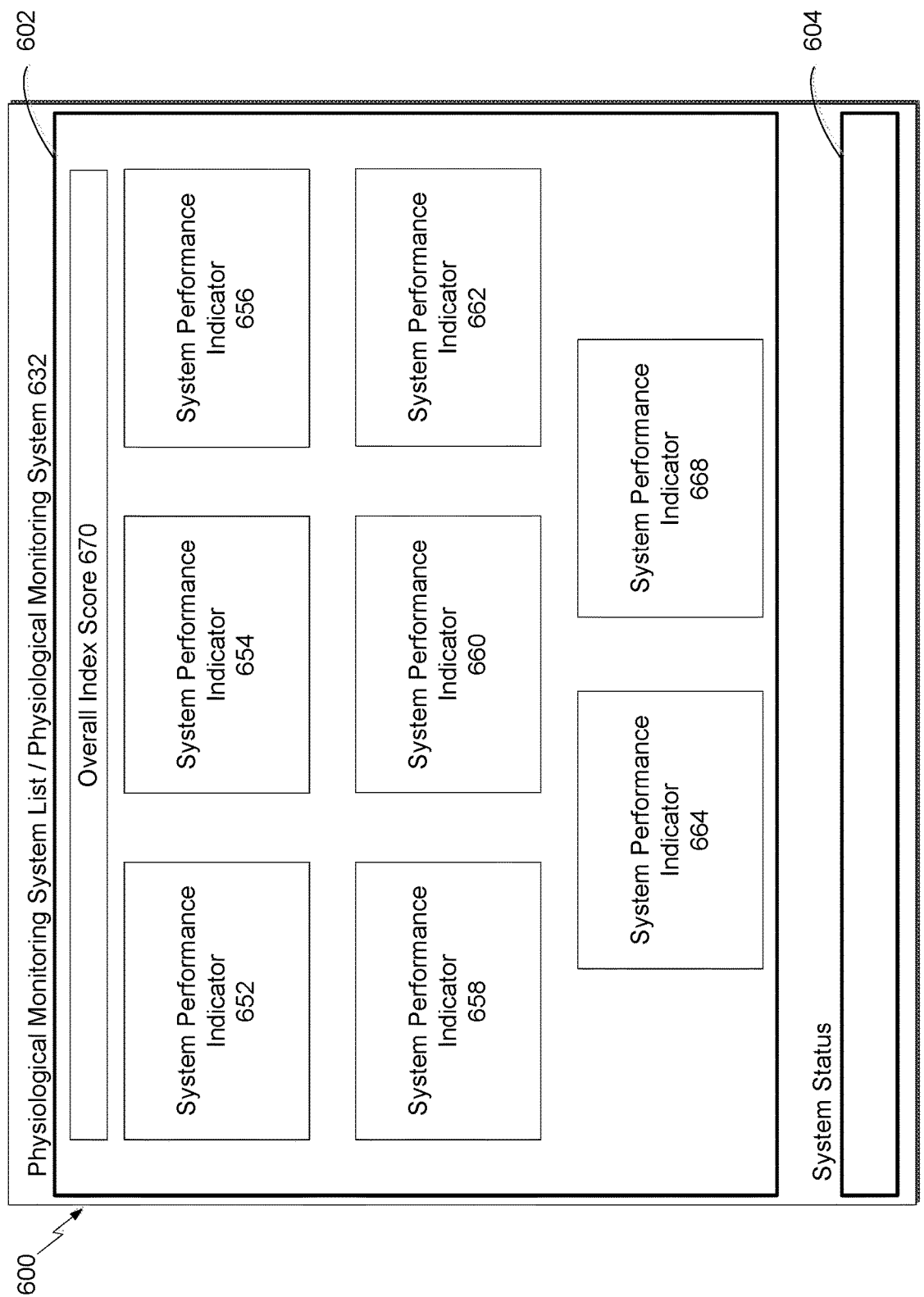

FIGS. 6A-C illustrate a network monitoring screen 600 that may be generated by a display module, such as display module 586 described herein with respect to FIG. 5. In certain embodiments, the network monitoring screen 600 may include a physiological monitoring system list pane 602 and/or a system status pane 604. In other embodiments, not shown, more or less information may be displayed within the network monitoring screen 600 and/or the physiological monitoring system list pane 602 and the system status pane 604 may be combined into one pane.

In certain embodiments, as illustrated in FIG. 6A, the physiological monitoring system list pane 602 includes a geographic region and one or more representations 606, 608, 610, and/or 612 of physiological monitoring systems. In some aspects, one or more representations 606, 608, 610, and/or 612 may represent a plurality of physiological monitoring systems. For example, representation 606 may symbolize the presence of three physiological monitoring systems (e.g., three different hospitals) within the geographic region where the representation 606 is located. As described herein, one or more representations 606, 608, 610, and/or 612 is selectable by a user. For example, a user may touch, press, click, hover over, type, speak, or otherwise choose a representation 606, 608, 610, or 612 and more information may displayed as described herein.

In certain embodiments, the system status pane 604 may display a notification when one is generated by the processor module 581. The system status pane 604 may indicate details of the notification and/or the representation 606, 608, 610, 612 and/or physiological monitoring system the notification is associated with.

In certain embodiments, as illustrated in FIG. 6B, once a representation 606, 608, 610, and/or 612 is selected, further information may be displayed within the physiological monitoring system list pane 602. For example, representation 606 may include 9 different physiological monitoring systems 632, 634, 636, 638, 640, 642, 644, 646, and/or 648. If representation 606 is chosen, representations of one or more of physiological monitoring systems 632, 634, 636, 638, 640, 642, 644, 646, and/or 648 may be displayed within the physiological monitoring system list pane 602. As an example, the representations of the physiological monitoring system 632, 634, 636, 638, 640, 642, 644, 646, and/or 648 may indicate a status of the respective physiological monitoring system. Such a status may be indicated graphically (e.g., via color coding based on whether the system is error free, whether the system is experiencing a few errors, and/or whether it is anticipated the system is or will face issues, etc.), numerically (e.g., index scores described below), or the like. Each of the representations of the physiological monitoring systems 632, 634, 636, 638, 640, 642, 644, 646, and/or 648 may be selectable (by a user) in ways as described herein to provide further information about the selected physiological monitoring system 632, 634, 636, 638, 640, 642, 644, 646, or 648.

As illustrated in FIG. 6C, upon selecting a representation of a physiological monitoring system 632, 634, 636, 638, 640, 642, 644, 646, or 648, the network monitoring screen 600 may display an index score for the chosen physiological monitoring system and/or indicators of clinical and/or system performance for the chosen physiological monitoring system. For example, if the representation of the physiological monitoring system 632 is selected, an overall index score 670 and eight indicators 652, 654, 656, 658, 660, 662, 664, and/or 668 may be displayed. In other embodiments, fewer or more indicators may be displayed.

The overall index score 670 may be a numerical representation of the overall health of the physiological monitoring system 632. For example, the overall index score 670 may range from zero to ten, with zero indicating that the physiological monitoring system 632 is performing poorly and ten indicating that the physiological monitoring system 632 is performing well, or vice-versa. In an embodiment, the processor module 581 calculates the overall index score 670 based on an individual index score generated for one or more of the indicators 652, 654, 656, 658, 660, 662, 664, and/or 668.

The processor module 581 may generate an individual index score for an indicator 652, 654, 656, 658, 660, 662, 664, or 668 based on a baseline value for the respective indicator and whether a current value for the respective indicator deviates from the baseline value. For example, a high index score may indicate that an indicator is performing well (e.g., the current value for the respective indicator is at or near the baseline value) and a low index score may indicate that an indicator is performing poorly (e.g., the current value for the respective indicator deviates from the baseline value by more than a threshold value), or vice-versa.

The overall index score 670 may be calculated based on the individual index scores of the indicators 652, 654, 656, 658, 660, 662, 664, and/or 668 and associated weights that are applied to the individual index scores. In an embodiment, the processor module 581 assigns weights to each indicator based on how much each indicator affects the overall performance of the physiological monitoring system 632. The weights may remain constant or may change over time. In one embodiment, the weights change based on a change in the current value of an indicator over a period of time. For example, a change in the value of an indicator and a change in the value of the indicator's weight may be directly or inversely proportional (e.g., if the value of an indicator increases by N %, the value of the weight may increase (or decrease) by N %). As another example, a change in the value of an indicator and a change in the value of the indicator's weight may have another type of relationship (e.g., a non-proportional relationship, a logarithmic relationship, a weight may change by a set value based on an amount of change in the value of the indicator, etc.).

As described herein with respect to FIGS. 7A-H, the indicators 652, 654, 656, 658, 660, 662, 664, and/or 668 may graphically (e.g., bar graphs, line graphs, charts, etc.) provide information about the selected physiological monitoring system 632. Additionally or in the alternative, the indicators 652, 654, 656, 658, 660, 662, 664, and/or 668 may graphically provide the individual index score for each respective indicator. In this way, by viewing the network monitoring screen 600, a user can immediately recognize which physiological monitoring systems are performing as expected, which physiological monitoring systems may face issues in the future, which physiological monitoring systems are currently facing issues, and which indicators may be responsible for any current or future issues.

Figure 7A:
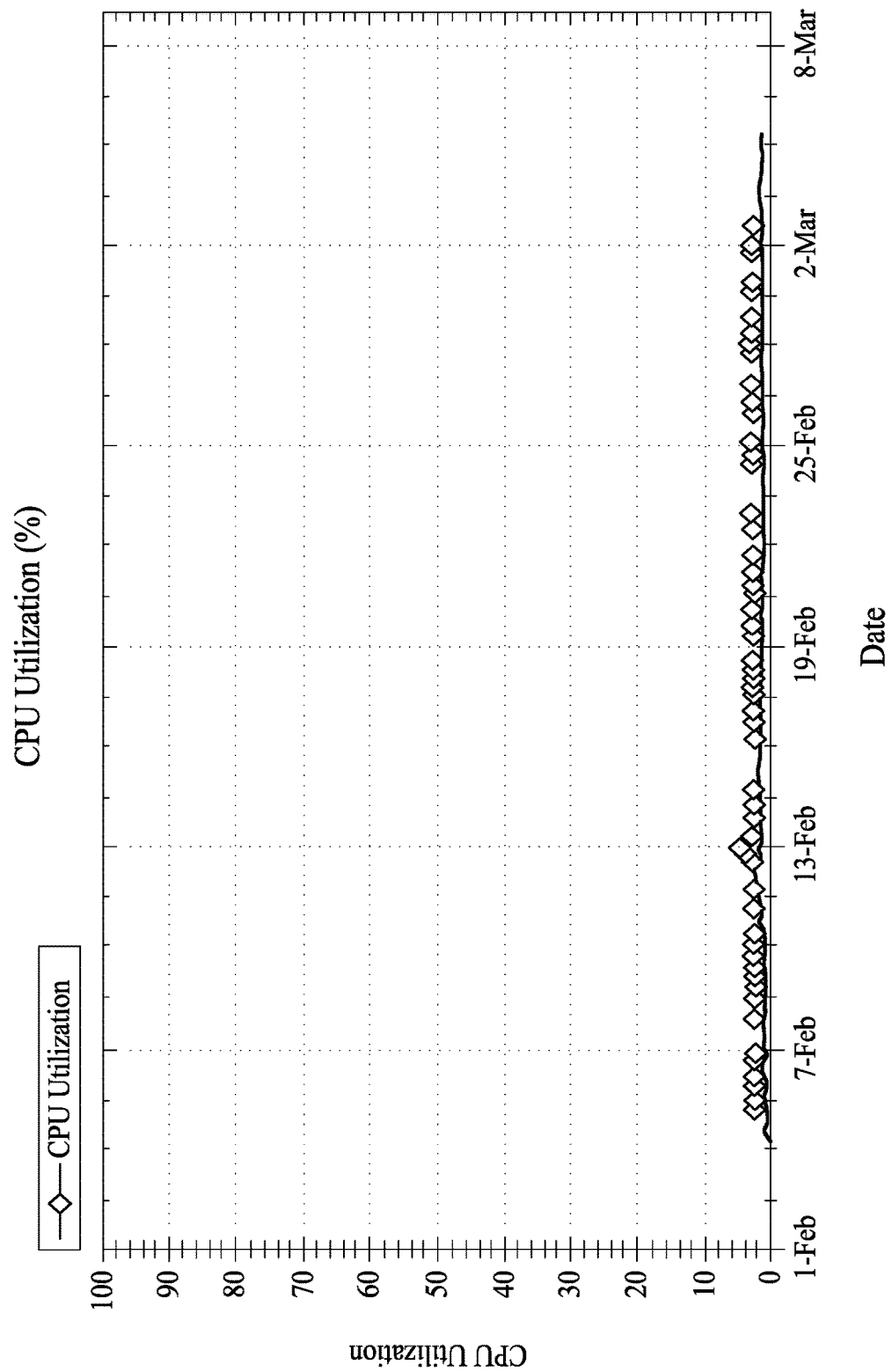
FIG. 7A is an exemplary indicator, such as one of the indicators of FIG. 6C.

FIG. 7A illustrates an example indicator, such as indicator 652 described herein with respect to FIG. 6C. Indicator 652 may graphically display the processor utilization (e.g., as a percentage) by the physiological monitoring system 632. Indicator 652 may provide such information as captured over a period of time. As illustrated in FIG. 7A, the processor utilization remains substantially constant, which may indicate that there are no current or upcoming issues.

Figure 7B:
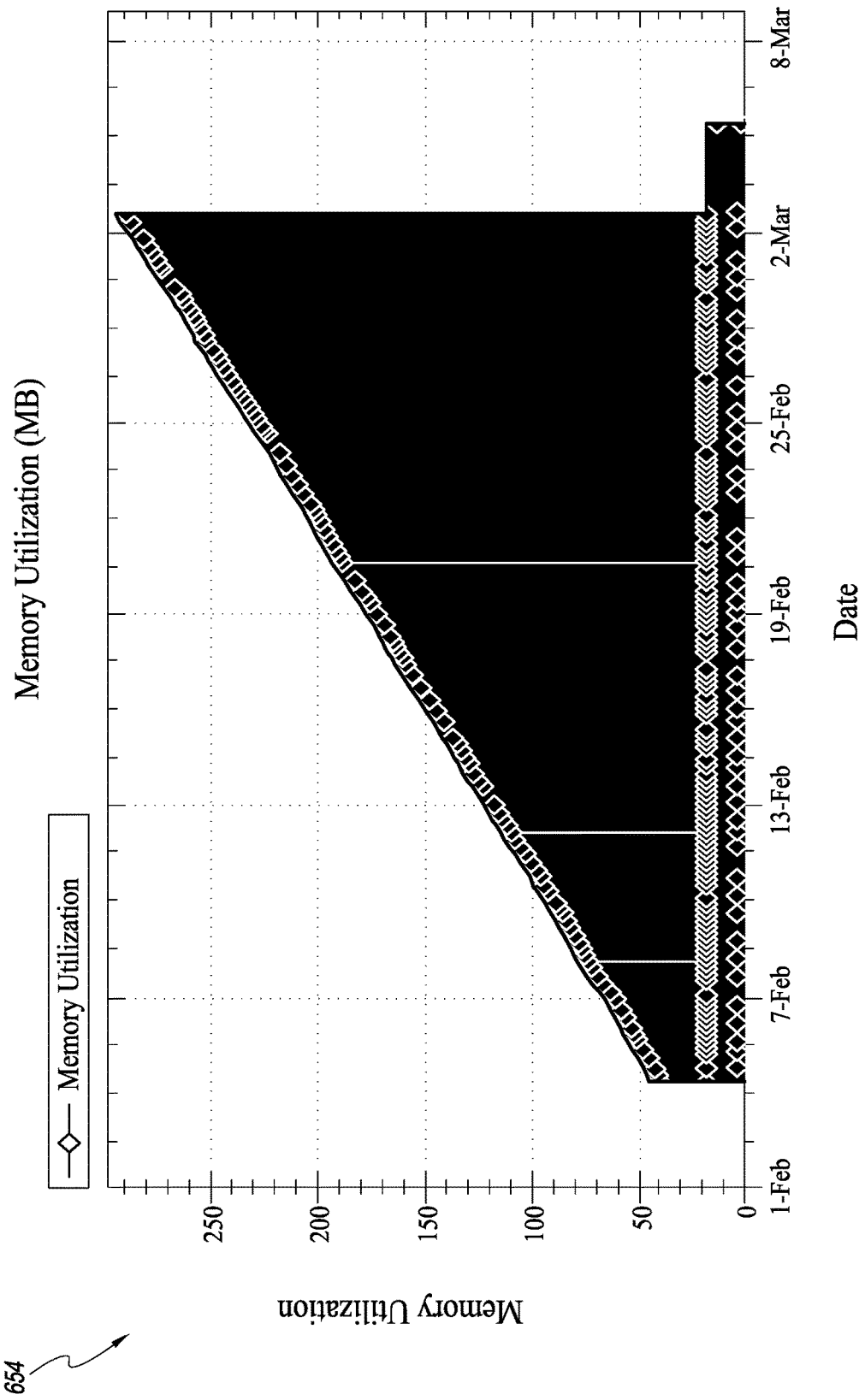
FIG. 7B is another exemplary indicator, such as one of the indicators of FIG. 6C.

FIG. 7B illustrates another example indicator, such as indicator 654 described herein with respect to FIG. 6C. Indicator 654 may graphically display the memory utilization (e.g., in megabytes) by the physiological monitoring system 632. Indicator 654 may provide such information as captured over a period of time. As illustrated in FIG. 7B, the memory utilization is steadily increasing, which may indicate that there is a current or upcoming problem with a device or other component in the physiological monitoring system 632. In such an instance, for example, the processor module 581 may generate a command to reset the physiological monitoring system 632.

Figure 7C:
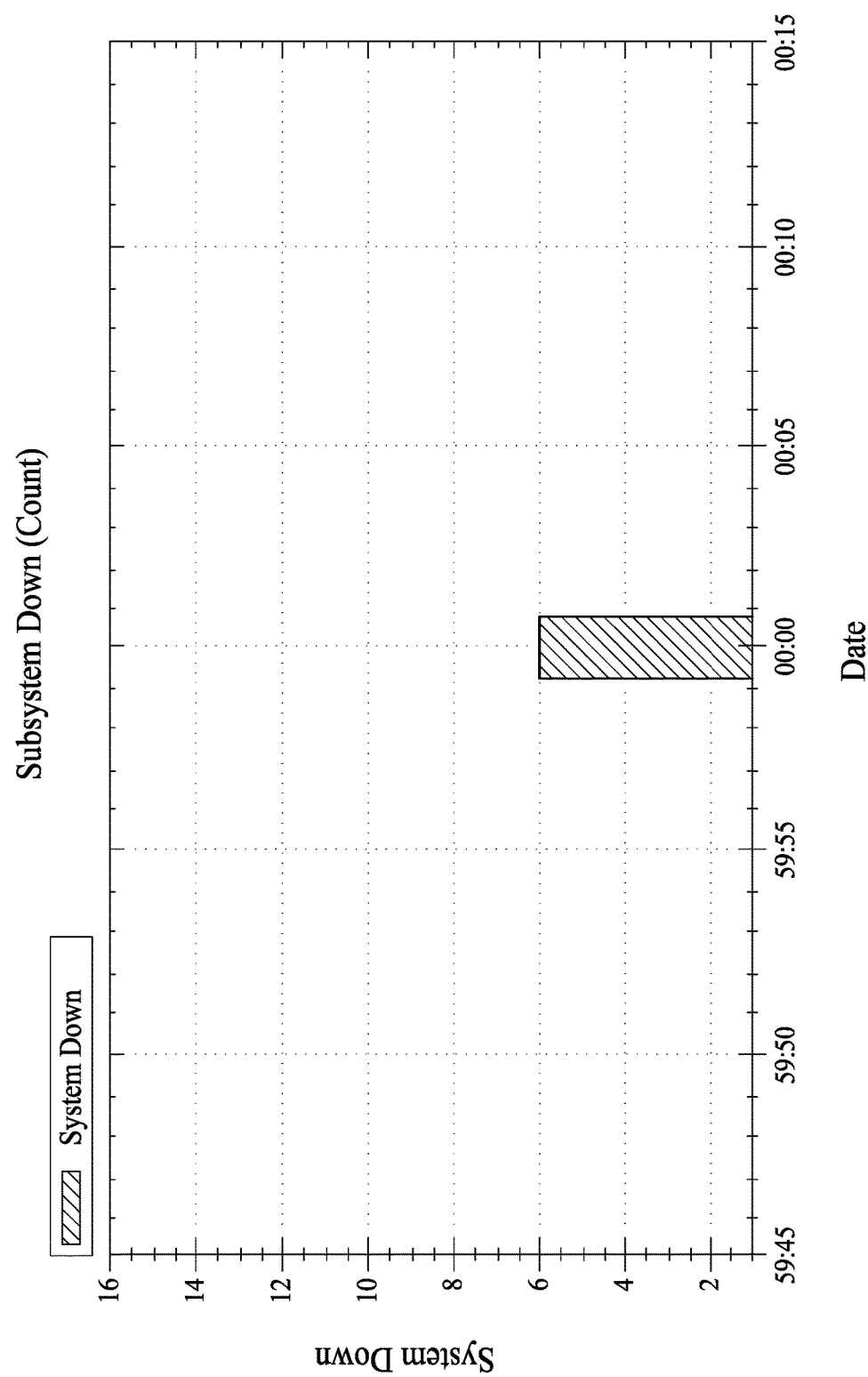
FIG. 7C is another exemplary indicator, such as one of the indicators of FIG. 6C.

FIG. 7C illustrates another example indicator, such as indicator 656 described herein with respect to FIG. 6C. Indicator 656 may graphically display the number of times a subsystem associated with the physiological monitoring system 632 failed. Indicator 656 may provide such information as captured over a period of time. As illustrated in FIG. 7C, the number of times the subsystem failed spiked at a given point in time, which may indicate that there is a current or upcoming problem and may lead to the generation of a notification.

Figure 7D:
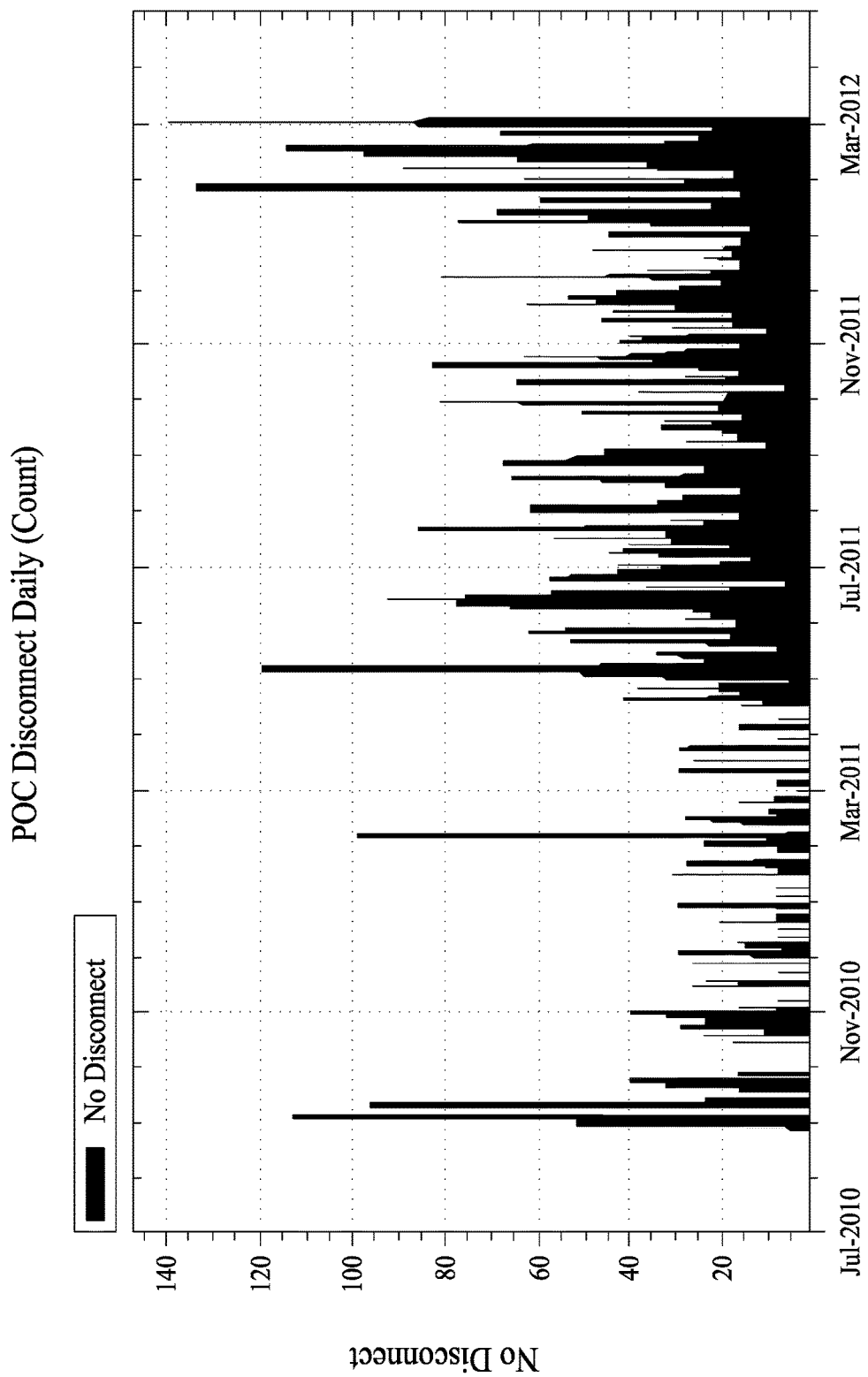
FIG. 7D is another exemplary indicator, such as one of the indicators of FIG. 6C.

FIG. 7D illustrates another example indicator, such as indicator 658 described herein with respect to FIG. 6C. Indicator 658 may graphically display the number of times a medical device disconnected from the physiological monitoring system 632. Indicator 658 may provide such information as captured over a period of time, such as a daily count. In certain embodiments, a baseline may be an average of the number of disconnects that occurred over a period of time. Deviations from the average may result in the generation of a notification.

Figure 7E:
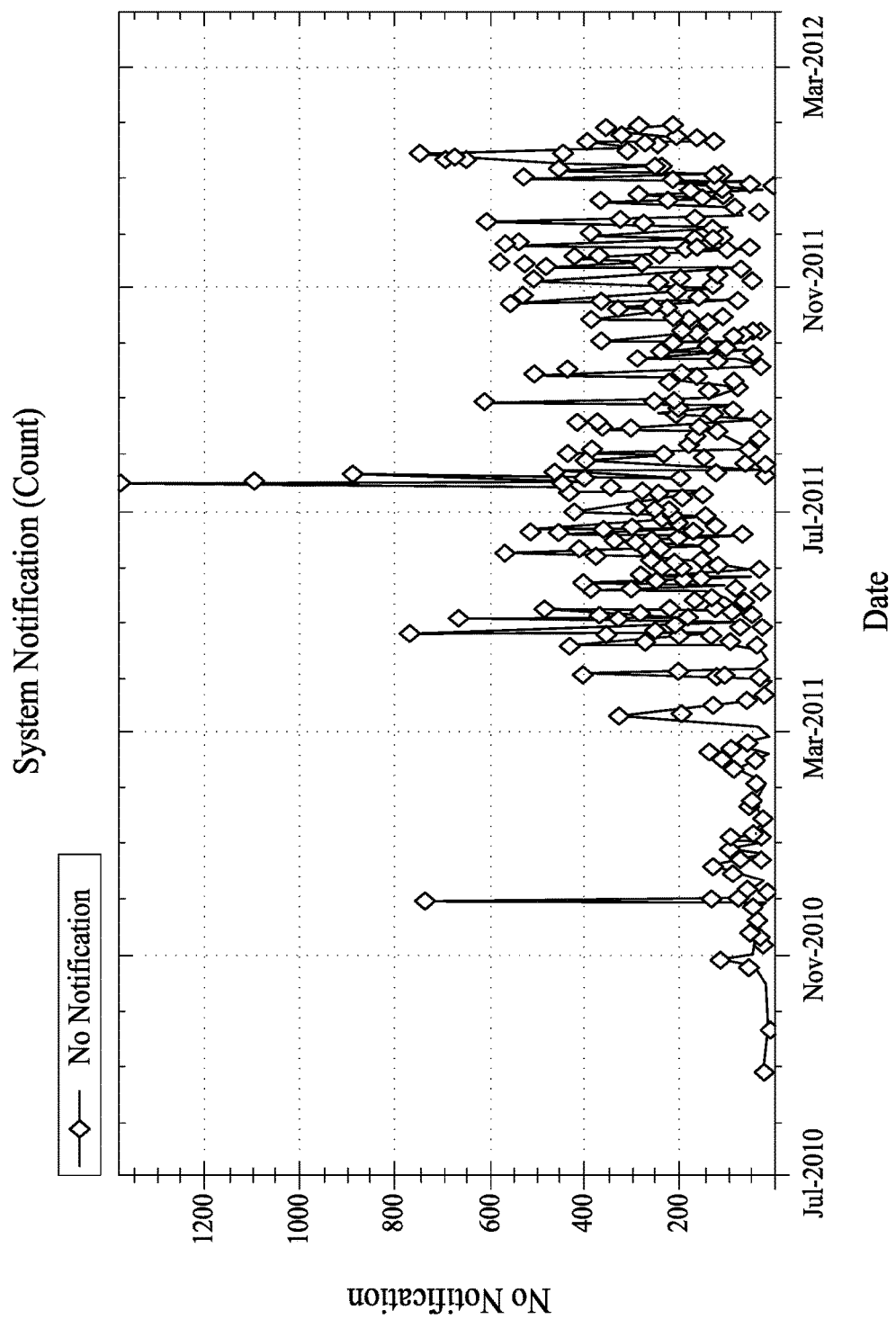
FIG. 7E is another exemplary indicator, such as one of the indicators of FIG. 6C.

FIG. 7E illustrates another example indicator, such as indicator 660 described herein with respect to FIG. 6C.

Indicator 660 may graphically display the number of times a medical device generated an alarm condition in the physiological monitoring system 632. Indicator 660 may provide such information as captured over a period of time. In certain embodiments, a baseline may be an average of the number of alarm conditions that occurred over a period of time. Deviations from the average may result in the generation of a notification.

Figure 7F:
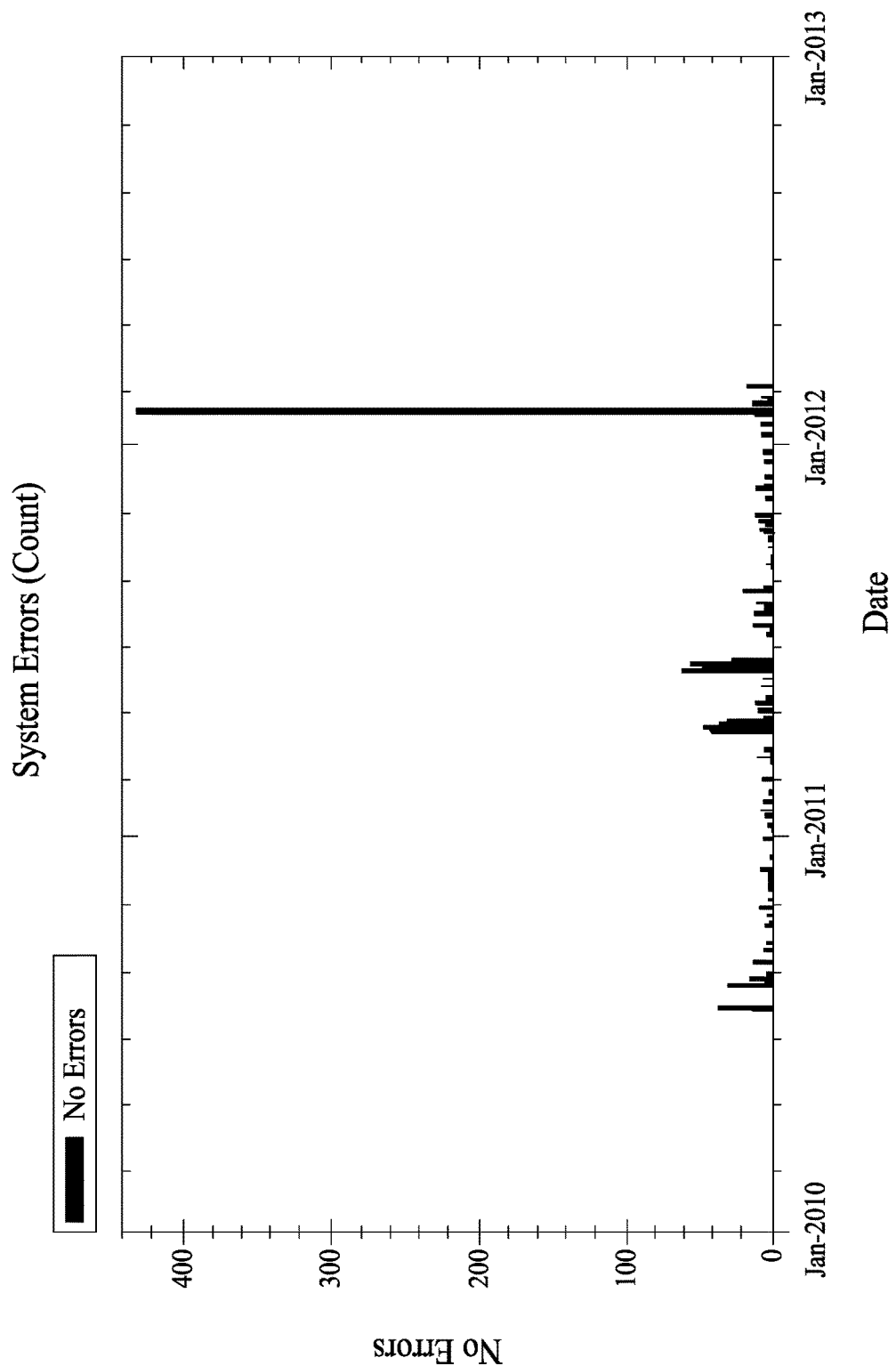
FIG. 7F is another exemplary indicator, such as one of the indicators of FIG. 6C.

FIG. 7F illustrates another example indicator, such as indicator 662 described herein with respect to FIG. 6C. Indicator 662 may graphically display the number of system errors in the physiological monitoring system 632. Indicator 662 may provide such information as captured over a period of time. In certain embodiments, a baseline may be an average of the number of system errors that occurred over a period of time. Deviations from the average may result in the generation of a notification.

Figure 7G:
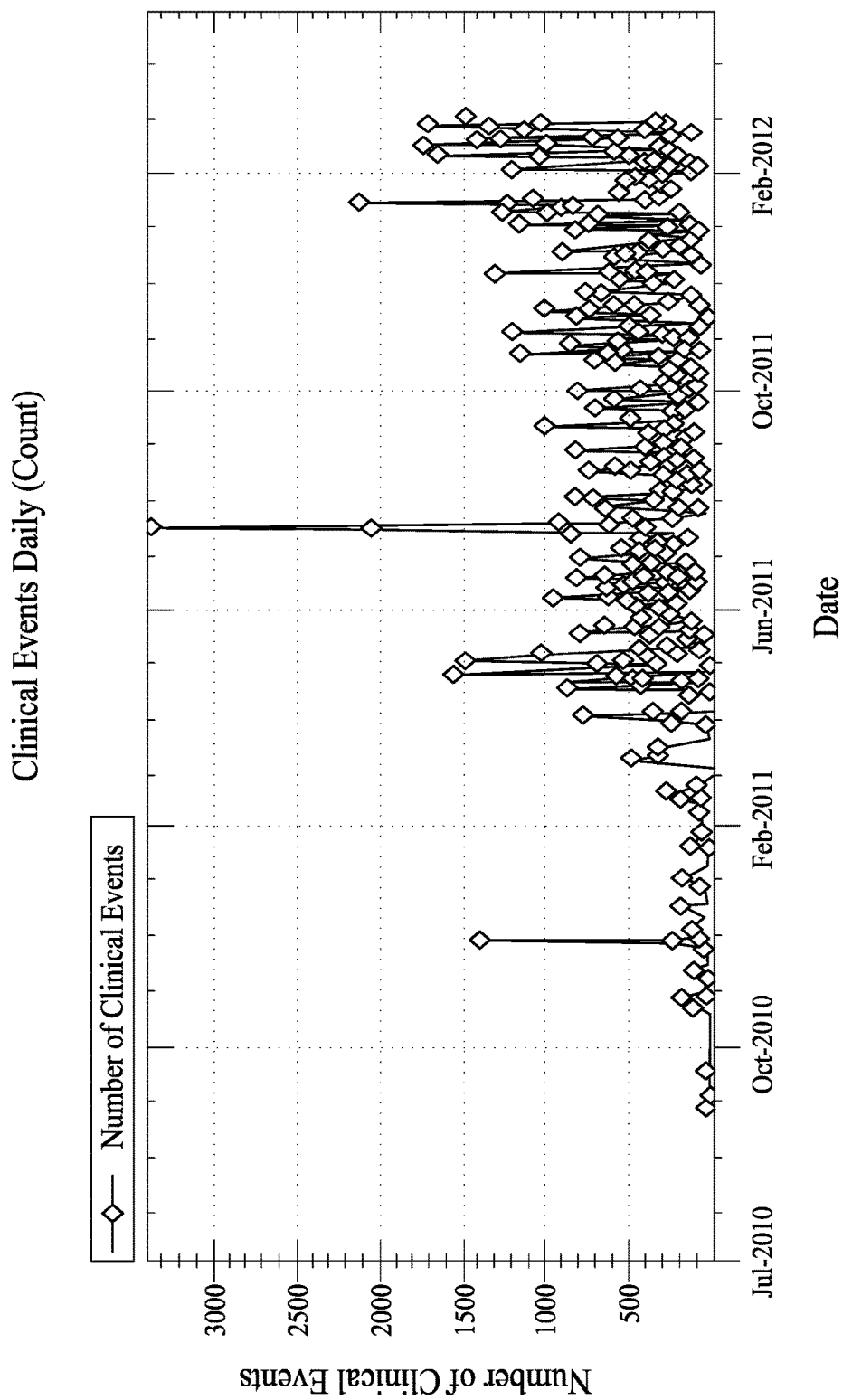
FIG. 7G is another exemplary indicator, such as one of the indicators of FIG. 6C.

FIG. 7G illustrates another example indicator, such as indicator 664 described herein with respect to FIG. 6C. Indicator 664 may graphically display the number of times a medical device within the physiological monitoring system 632 generated an alarm condition that lasted more than a predetermined amount of time. Indicator 664 may provide such information as captured over a period of time. In certain embodiments, a baseline may be an average of the number of alarm conditions that lasted more than the predetermined amount of time that occurred over a period of time. Deviations from the average may result in the generation of a notification.

Figure 7H:
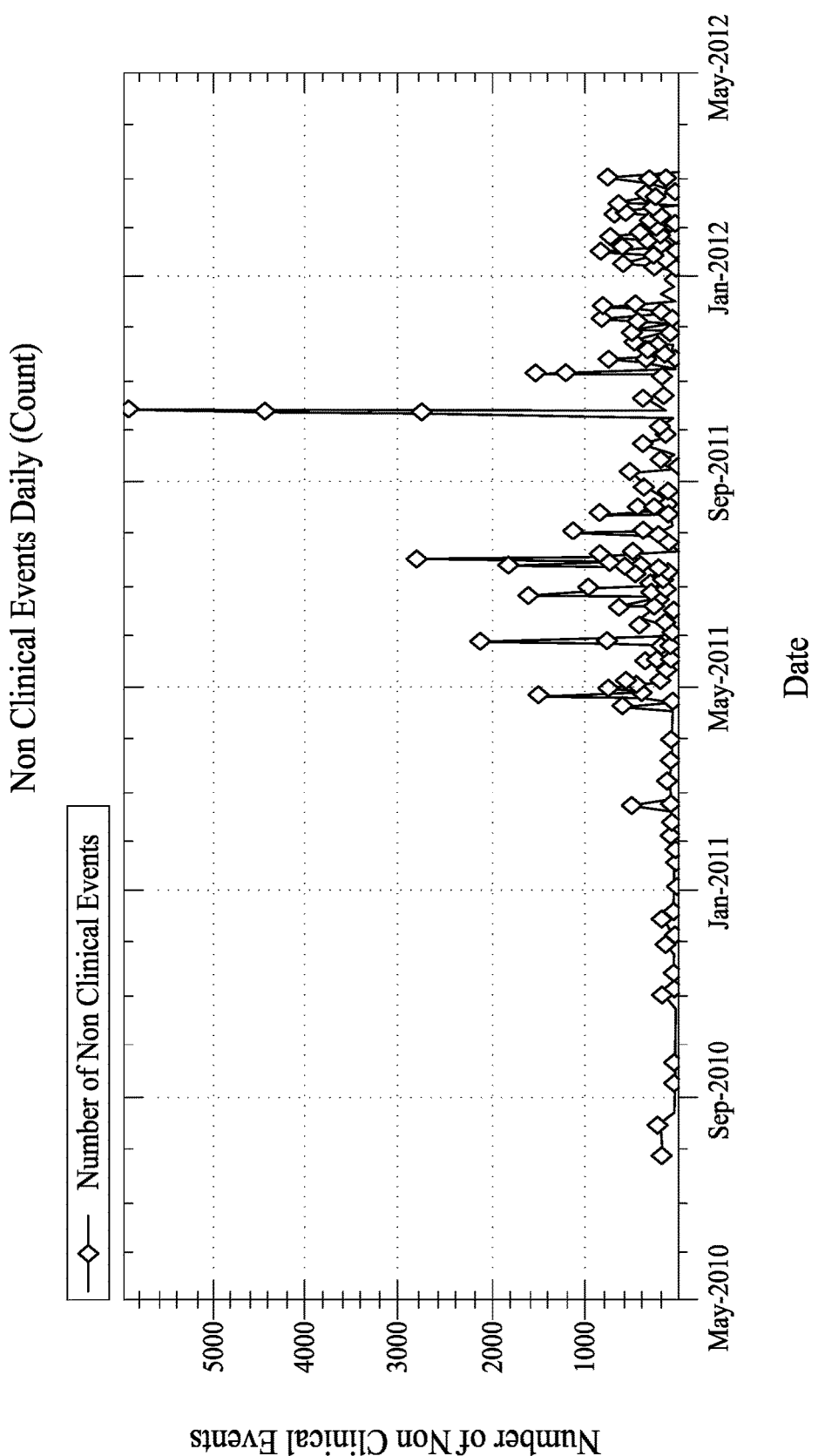
FIG. 7H is another exemplary indicator, such as one of the indicators of FIG. 6C.

FIG. 7H illustrates another example indicator, such as indicator 668 described herein with respect to FIG. 6C. Indicator 668 may graphically display the number of times a medical device within the physiological monitoring system 632 generated an alarm condition that lasted less than the predetermined amount of time. Indicator 668 may provide such information as captured over a period of time. In certain embodiments, a baseline may be an average of the number of alarm conditions that lasted less than the predetermined amount of time that occurred over a period of time. Deviations from the average may result in the generation of a notification.

Figure 8:
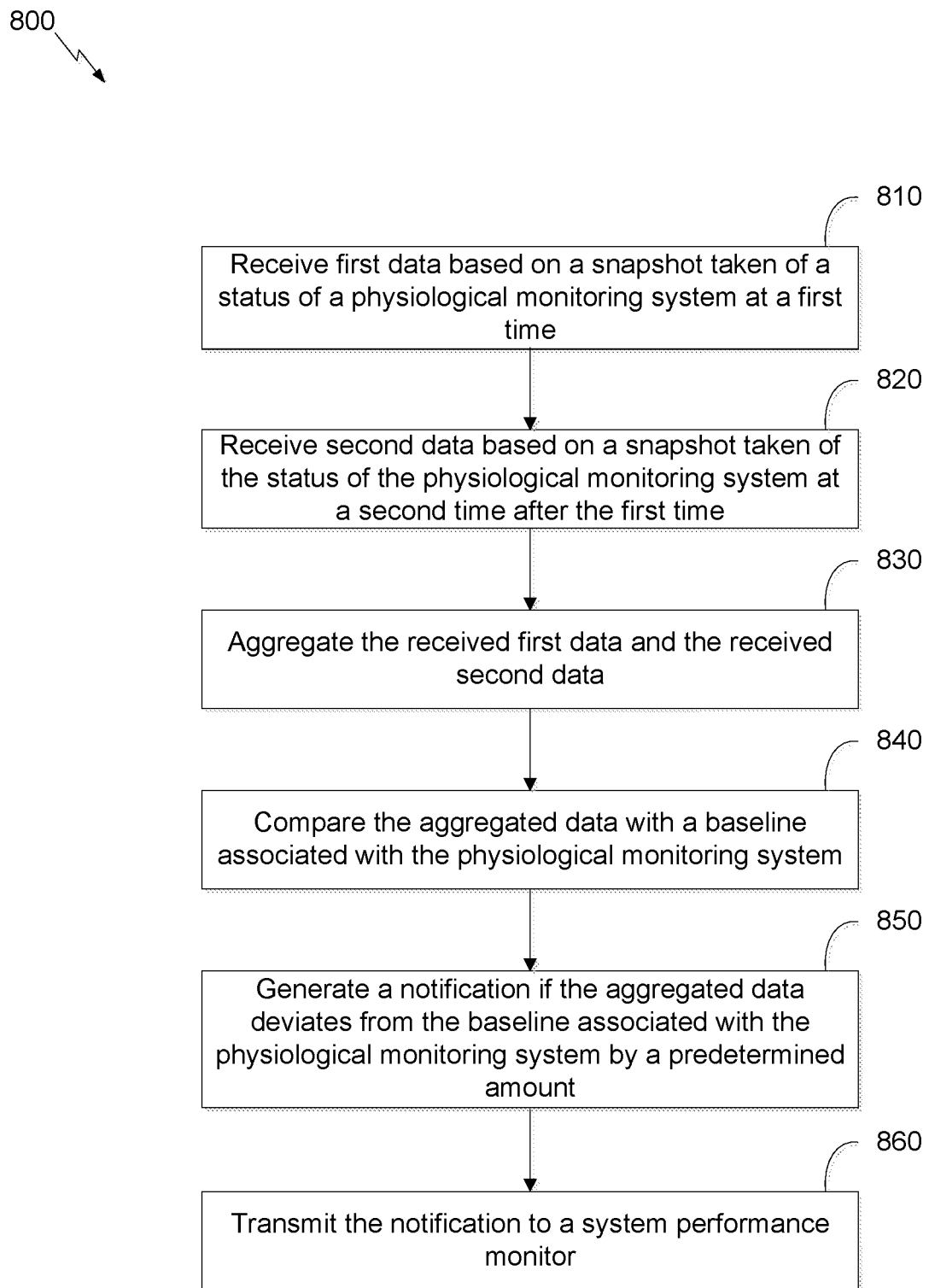
FIG. 8 is a flowchart that illustrates a process for identifying a change in system performance in a physiological monitoring system, such as the physiological monitoring system of FIG. 1.

FIG. 8 illustrates an embodiment of a process 800 for identifying a change in system performance in a physiological monitoring system. In various embodiments, additional blocks may be performed, fewer blocks than shown may be performed, and/or the blocks may be performed in an order different than that shown. The process may be performed, for example, by the network monitoring server 572 of FIG. 4.

In an embodiment, the process 800 begins at block 810. At block 810, first data based on a snapshot taken of a status of a physiological monitoring system at a first time is received. In an embodiment, the status of the physiological monitoring system comprises at least one indicator of a clinical and/or system performance of the physiological monitoring system. In some embodiments, after block 810, the process 800 proceeds to block 820. At block 820, second data based on a snapshot taken of a status of a physiological monitoring system at a second time after the first time is received. In some embodiments, after block 820, the process 800 proceeds to block 830. At block 830, the first data and the second data is aggregated. In an embodiment, like indicators of clinical and/or system performance are aggregated. In some embodiments, after block 830, the process 800 proceeds to block 840.

At block 840, the aggregated data is compared with a baseline associated with the physiological monitoring system. In an embodiment, like indicators of clinical and/or system performance are compared. In some embodiments, after block 840, the process 800 proceeds to block 850. At block 850, a notification is generated if the aggregated data deviates from the baseline by a predetermined amount. In an embodiment, the predetermined amount may be an absolute numerical value, a percentage, and/or the like. In some embodiments, after block 850, the process 800 proceeds to block 860. At block 860, the notification is transmitted to a system performance monitor. In an embodiment, the notification may include a command or instructions to perform an operation. In further embodiments, the notification identifies the medical device or other component of the physiological monitoring system that may be causing the problem. In further embodiments, the system performance monitor is one of a computing device within the physiological monitoring system or a computing device outside of the physiological monitoring system (e.g., a network monitoring server).

Information and signals described herein can be represented using any of a variety of different technologies and techniques. For example, data, instructions, commands, information, signals, bits, symbols, and chips that can be referenced throughout the above description can be represented by voltages, currents, electromagnetic waves, magnetic fields or particles, optical fields or particles, or any combination thereof.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans can implement the described functionality in varying ways for each particular application, but such implementation decisions should not be interpreted as causing a departure from the scope of the present invention.

Depending on the embodiment, certain acts, events, or functions of any of the methods described herein can be performed in a different sequence, may be added, merged, or left out altogether (e.g., not all described acts or events are necessary for the practice of the method). Moreover, in certain embodiments, acts or events may be performed concurrently, e.g., through multi-threaded processing, interrupt processing, or multiple processors, rather than sequentially.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, conventional processor, controller, microcontroller, state machine, etc. A processor can also be implemented as a combination of computing devices, e.g., a combination of a DSP and a microprocessor, a plurality of microprocessors, one or more microprocessors in conjunction with a DSP core, or any other such configuration. In addition, the term "processing" is a broad term meant to encompass several meanings including, for example, implementing program code, executing instructions, manipulating signals, filtering, performing arithmetic operations, and the like.

The steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, a DVD, or any other form of storage medium known in the art. A storage medium is coupled to the processor such that the processor can read information from, and write information to, the storage medium. In the alternative, the storage medium may be integral to the processor. The processor and the storage medium can reside in an ASIC. The ASIC can reside in a user terminal. In the alternative, the processor and the storage medium can reside as discrete components in a user terminal.

The modules can include, but are not limited to, any of the following: software or hardware components such as software object-oriented software components, class components and task components, processes, methods, functions, attributes, procedures, subroutines, segments of program code, drivers, firmware, microcode, circuitry, data, databases, data structures, tables, arrays, or variables.

In addition, although this invention has been disclosed in the context of certain preferred embodiments, it should be understood that certain advantages, features and aspects of the systems, devices, and methods may be realized in a variety of other embodiments. Additionally, it is contemplated that various aspects and features described herein can be practiced separately, combined together, or substituted for one another, and that a variety of combination and subcombinations of the features and aspects can be made and still fall within the scope of the invention. Furthermore, the systems and devices described above need not include all of the modules and functions described in the preferred embodiments.

What is claimed is:

1. A method comprising:
   as implemented by a network monitoring system comprising computer hardware and memory, the network monitoring system configured with specific executable instructions,
   receiving, from a first physiological monitoring system in a plurality of physiological monitoring systems, first data based on at least one indicator of a system performance of a component of the first physiological monitoring system, wherein the first physiological monitoring system comprises the component and one or more patient monitoring devices, wherein the one or more patient monitoring devices each comprise one or more sensors configured to obtain physiological information when coupled to a patient, the one or more patient monitoring devices configured to communicate via a network associated with the first physiological monitoring system;
   determining that the received first data satisfies a first condition;
   generating a notification in response to the determination that the received first data satisfies the first condition; and
   causing display of information associated with individual physiological monitoring systems of the plurality of physiological monitoring systems and the notification.

2. The method of claim 1, further comprising:
   receiving, from the first physiological monitoring system, second data based on a snapshot taken of the at least one indicator of the system performance of the component;
   aggregating the received first data and the received second data;
   determining that the aggregated data satisfies the first condition; and
   generating the notification in response to the determination that the aggregated data satisfies the first condition.

3. The method of claim 1, further comprising:
   receiving, from the first physiological monitoring system, second data based on a snapshot taken of the at least one indicator of the system performance of the component; and
   generating a baseline associated with the component based on the received second data.

4. The method of claim 1, wherein the receiving first data comprises receiving at least one of a processor utilization by the component, a memory utilization by the component, a number of times a notification system associated with the first physiological monitoring system failed, a number of times at least one first medical device disconnected from the first physiological monitoring system, a number of times at least one second medical device generated an alarm condition, a number of errors generated by the component, a number of times the at least one second medical device generated the alarm condition that lasted more than a threshold amount of time, or a number of times the at least one second medical device generated the alarm condition that lasted less than the threshold amount of time.

5. The method of claim 1, further comprising transmitting a message to a system performance monitor identifying the component.

6. The method of claim 5, wherein the system performance monitor is one of a computing device internal to the first physiological monitoring system or a computing device external to the first physiological monitoring system.

7. The method of claim 1, wherein determining that the received first data satisfies the first condition further comprises determining that there is one of a current problem associated with the component or a problem with the component that will occur at a future time.

8. The method of claim 1, further comprising generating a command to reset the first physiological monitoring system.

9. The method of claim 1, further comprising causing display of the received first data in response to a selection of the information associated with the first physiological monitoring system.

10. The method of claim 1, wherein the notification comprises content indicating how to resolve an issue associated with the first physiological monitoring system.

11. A system comprising:
    a communication interface configured to receive, from a first physiological monitoring system in a plurality of physiological monitoring systems, first data based on at least one indicator of a system performance of a component of the first physiological monitoring system, wherein the first physiological monitoring system comprises the component and one or more patient monitoring devices, wherein the one or more patient monitoring devices each comprise one or more sensors configured to obtain physiological information when coupled to a patient, the one or more patient monitoring devices configured to communicate via a network associated with the first physiological monitoring system;
memory configured to store the received first data; and
a processor configured to determine that the received first data satisfies a first condition, to generate a notification in response to the determination that the received first data satisfies the first condition, and to cause a display to display information associated with individual physiological monitoring systems of the plurality of physiological monitoring systems and the notification.

12. The system of claim 11, wherein the communication interface is further configured to receive, from the first physiological monitoring system, second data based on a snapshot taken of the at least one indicator of the system performance of the component.

13. The system of claim 12, wherein the processor is further configured to aggregate the received first data and the received second data, to determine that the aggregated data satisfies the first condition, and to generate the notification in response to the determination that the aggregated data satisfies the first condition.

14. The system of claim 12, wherein the processor is further configured to generate a baseline associated with the component based on the received second data.

15. The system of claim 11, wherein the first data comprises at least one of a processor utilization by the component, a memory utilization by the component, a number of times a notification system associated with the first physiological monitoring system failed, a number of times at least one first medical device disconnected from the first physiological monitoring system, a number of times at least one second medical device generated an alarm condition, a number of errors generated by the component, a number of times the at least one second medical device generated the alarm condition that lasted more than a threshold amount of time, or a number of times the at least one second medical device generated the alarm condition that lasted less than the threshold amount of time.

16. The system of claim 11, wherein the communication interface is further configured to transmit to a system performance monitor a message identifying the component.

17. The system of claim 11, wherein the processor is further configured to determine that there is one of a current problem associated with the component or a problem with the component that will occur at a future time.

18. The system of claim 11, wherein the processor is further configured to generate a command to reset the first physiological monitoring system.

19. The system of claim 11, wherein the display is caused to display the received first data in response to a selection of the information associated with the first physiological monitoring system.

20. The system of claim 11, wherein the notification comprises content indicating how to resolve an issue with the first physiological monitoring system.

\* \* \* \* \*